United States Patent [19]
Huebner

[11] Patent Number: 5,964,768
[45] Date of Patent: Oct. 12, 1999

[54] TAPERED BONE SCREW WITH CONTINUOUSLY VARYING PITCH

[75] Inventor: Randall J. Huebner, Aloha, Oreg.

[73] Assignee: Acumed, Inc., Beaverton, Oreg.

[21] Appl. No.: 09/034,046

[22] Filed: Mar. 3, 1998

Related U.S. Application Data

[63] Continuation-in-part of application No. 08/781,571, Jan. 10, 1997, and a continuation-in-part of application No. PCT/US94/00738, Jan. 19, 1994, said application No. 08/781,571, is a continuation-in-part of application No. 08/506,469, Jul. 25, 1995, which is a continuation-in-part of application No. 08/332,445, Oct. 31, 1994, Pat. No. 5,562,672, which is a continuation of application No. 08/007,196, Jan. 21, 1993.

[51] Int. Cl.$^6$ .................................................. A61B 17/56
[52] U.S. Cl. .............................. 606/73; 606/72; 606/75; 606/65; 606/105; 411/115; 411/423; 411/426; 411/307
[58] Field of Search ................................ 606/73, 72, 74, 606/75, 59–65, 104, 105; 411/415, 423, 426, 307; 433/173

[56] References Cited

U.S. PATENT DOCUMENTS

| | | |
|---|---|---|
| 65,651 | 6/1867 | Davies . |
| 146,023 | 12/1873 | Russell ................................ 411/415 |
| 197,467 | 11/1877 | Harvey . |
| 197,933 | 12/1877 | Harvey . |
| D. 356,868 | 3/1995 | Broberg et al. . |
| 1,980,093 | 11/1934 | Rosenberg . |
| 2,146,023 | 12/1939 | Russell . |
| 2,165,149 | 7/1939 | Olson . |
| 2,356,098 | 8/1944 | Steinle et al. . |
| 2,377,405 | 6/1945 | Davies . |
| 2,382,019 | 8/1945 | Miller . |
| 2,383,231 | 8/1945 | Anderton . |
| 2,419,555 | 4/1947 | Fator . |
| 2,633,091 | 3/1953 | Wenger et al. . |
| 2,801,631 | 8/1957 | Charnley . |
| 2,842,180 | 7/1958 | Brown et al. . |
| 3,051,169 | 8/1962 | Grath . |

(List continued on next page.)

FOREIGN PATENT DOCUMENTS

| | | |
|---|---|---|
| 731381 | 4/1966 | Canada . |
| 1007493 | 3/1977 | Canada . |
| 0172130 | 2/1986 | European Pat. Off. . |

(List continued on next page.)

OTHER PUBLICATIONS

The Herbert™ Bone Screws for Small Bone Fractures, Fracture Management, 97–1152–01 12.5MI Printed in U.S.A.© 1992 Zimmer, Inc.

Toby et al., "A Comparison of Fixation Screws for the Scaphoid During Application of Cyclical Bending Loads," *Journal of Bone and Joint Surgery*, vol. 79–A, No. 8, pp. 1190–1197, Aug. 1997.

Haddad et al., "Acute Percutaneous Scaphoid Fixation," *The Journal of Bone and Joint Surgery*, vol. 80–B, No. 1, pp. 95–99, Jan. 1998.

Wheeler et al., "Biomechanical Assessment of Compression Screws," *Clinical Orthopaedics and Related Research*, No. 350, pp. 237–245, May 1998.

*Primary Examiner*—Michael Buiz
*Assistant Examiner*—Lien Ngo
*Attorney, Agent, or Firm*—Kolisch, Hartwell, Dickinson, McCormack & Heuser

[57] ABSTRACT

A bone screw having a continuously varying pitch includes a tapered root portion having a relatively small diameter on a leading end of the screw and a larger trailing diameter. The pitch of the screw decreases between the leading and trailing ends thus causing the bone fragments in a fracture to be drawn together when the screw is installed across the fragments. The radially outer diameter of the threads increases between the leading and trailing ends thus causing each successive thread portion to cut into bone radially outwardly from the preceding thread portion thereby providing uncut bone in which the succeeding threads can gain purchase.

35 Claims, 13 Drawing Sheets

U.S. PATENT DOCUMENTS

| | | |
|---|---|---|
| 3,079,181 | 2/1963 | van der Wissel . |
| 3,124,408 | 3/1964 | Oestereicher . |
| 3,233,500 | 2/1966 | de Vellier . |
| 3,454,070 | 7/1969 | Phipard, Jr. . |
| 3,664,540 | 5/1972 | Witkin . |
| 3,799,229 | 3/1974 | Johnson . |
| 3,915,162 | 10/1975 | Miller . |
| 4,058,856 | 11/1977 | Doerre et al. . |
| 4,059,102 | 11/1977 | Devas . |
| 4,069,980 | 1/1978 | Yarem et al. . |
| 4,175,555 | 11/1979 | Herbert . |
| 4,340,184 | 7/1982 | Poss . |
| 4,456,005 | 6/1984 | Lichty . |
| 4,463,753 | 8/1984 | Gustilo . |
| 4,468,200 | 8/1984 | Munch . |
| 4,537,185 | 8/1985 | Stednitz . |
| 4,640,271 | 2/1987 | Lower . |
| 4,723,541 | 2/1988 | Reese . |
| 4,842,464 | 6/1989 | Green . |
| 4,854,311 | 8/1989 | Steffee . |
| 4,863,383 | 9/1989 | Grafelmann . |
| 4,892,429 | 1/1990 | Giannuzzi . |
| 4,917,554 | 4/1990 | Bronn . |
| 4,940,467 | 7/1990 | Tronzo . |
| 4,950,270 | 8/1990 | Bowman et al. . |
| 4,959,064 | 9/1990 | Engelhardt . |
| 5,019,078 | 5/1991 | Perren et al. . |
| 5,019,079 | 5/1991 | Ross . |
| 5,042,982 | 8/1991 | Harms et al. . |
| 5,120,171 | 6/1992 | Lasner . |
| 5,147,363 | 9/1992 | Harle . |
| 5,180,382 | 1/1993 | Frigg et al. . |
| 5,252,016 | 10/1993 | Schmid et al. . |
| 5,259,398 | 11/1993 | Vrespa ..................................... 606/65 |
| 5,300,076 | 4/1994 | Leriche . |
| 5,306,275 | 4/1994 | Bryan . |
| 5,403,136 | 4/1995 | Mathys . |
| 5,470,334 | 11/1995 | Ross et al. . |
| 5,484,440 | 1/1996 | Allard . |
| 5,536,127 | 7/1996 | Pennig . |
| 5,569,252 | 10/1996 | Justin et al. . |
| 5,571,139 | 11/1996 | Jenkins, Jr. . |
| 5,730,744 | 3/1998 | Justin et al. . |
| 5,743,912 | 4/1998 | Lahille et al. . |
| 5,779,704 | 7/1998 | Kim . |

FOREIGN PATENT DOCUMENTS

| | | |
|---|---|---|
| 2588332 | of 0000 | France . |
| 2618344 | of 0000 | Germany . |
| 3215228A1 | 11/1983 | Germany . |
| 3630863A1 | 3/1988 | Germany . |
| 4021550A1 | 1/1991 | Germany . |
| 365613 | of 0000 | Italy . |
| 598490 | of 0000 | Italy . |
| 4524729 | of 0000 | Japan . |
| 77837 | of 0000 | Switzerland . |
| 1216466 | of 0000 | U.S.S.R. . |
| 178877 A1 | of 0000 | U.S.S.R. . |
| 1034734 | 8/1983 | U.S.S.R. . |
| 1389427 | 11/1972 | United Kingdom . |
| 89/9030 | of 0000 | WIPO . |
| WO90/02526 | 3/1990 | WIPO . |
| WO93/00518 | 1/1993 | WIPO . |

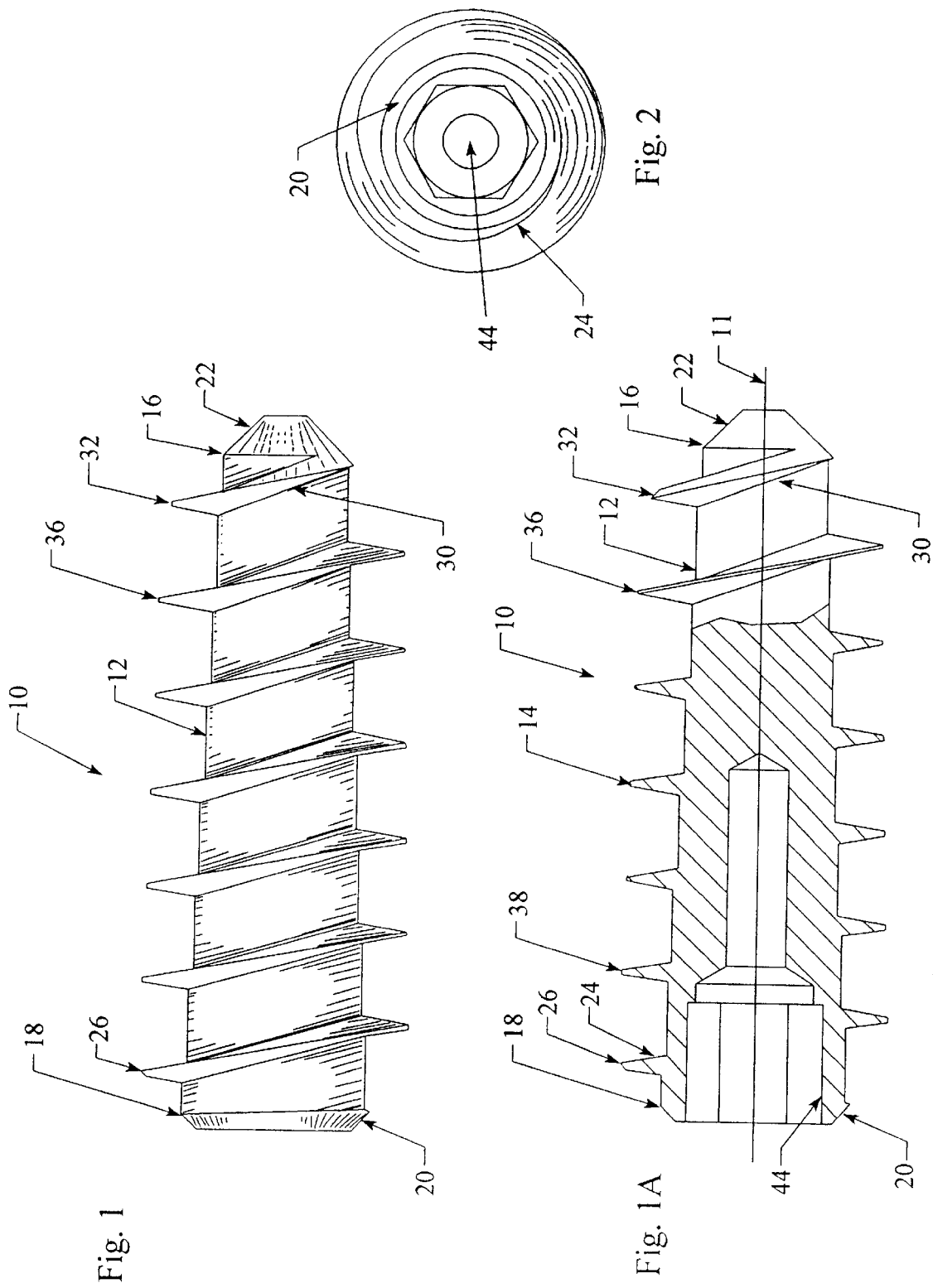

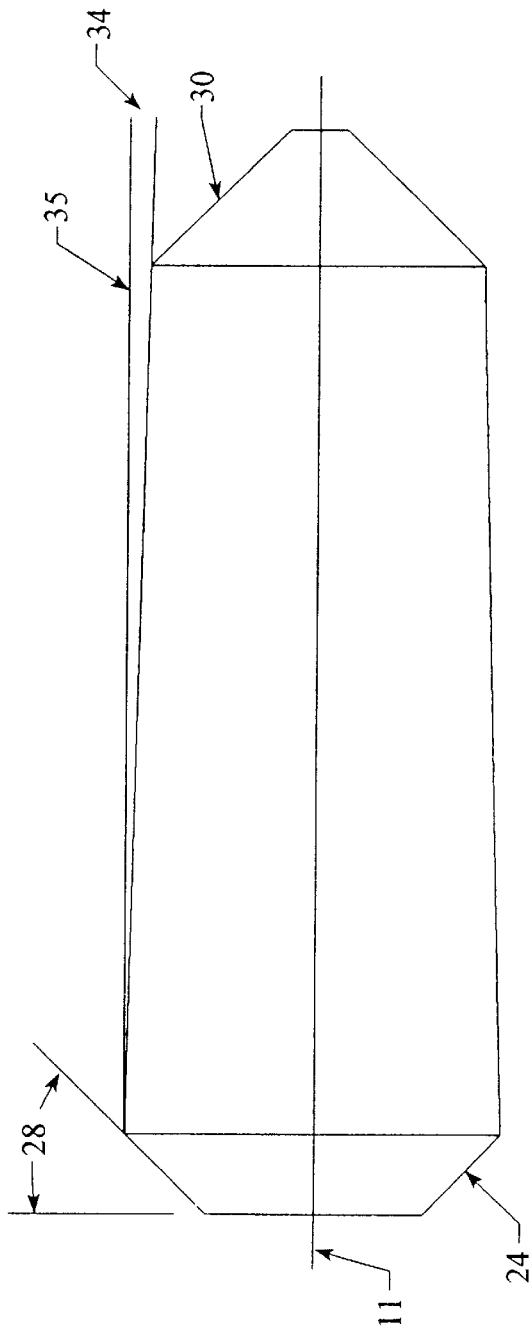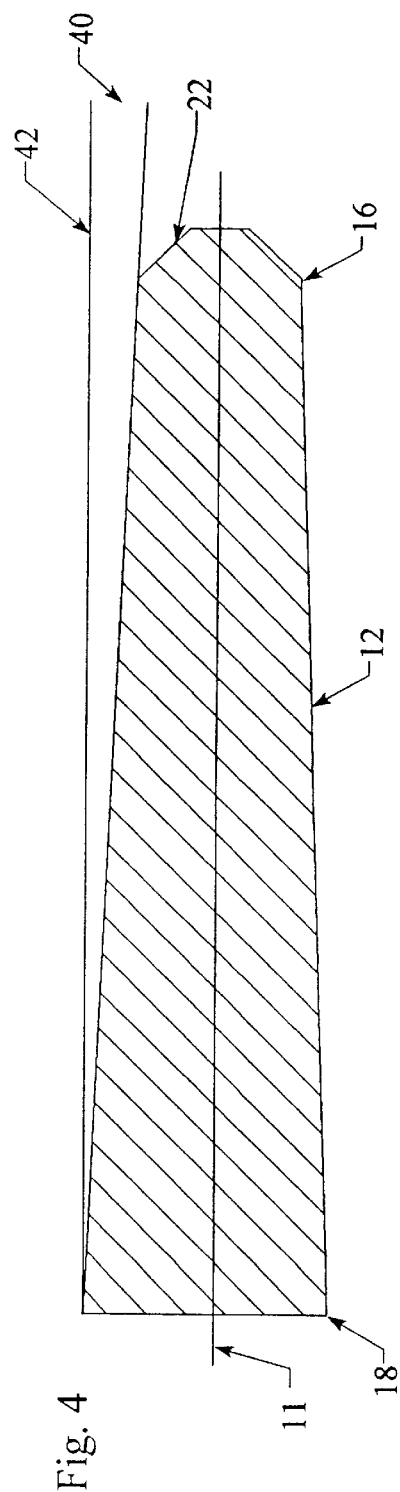

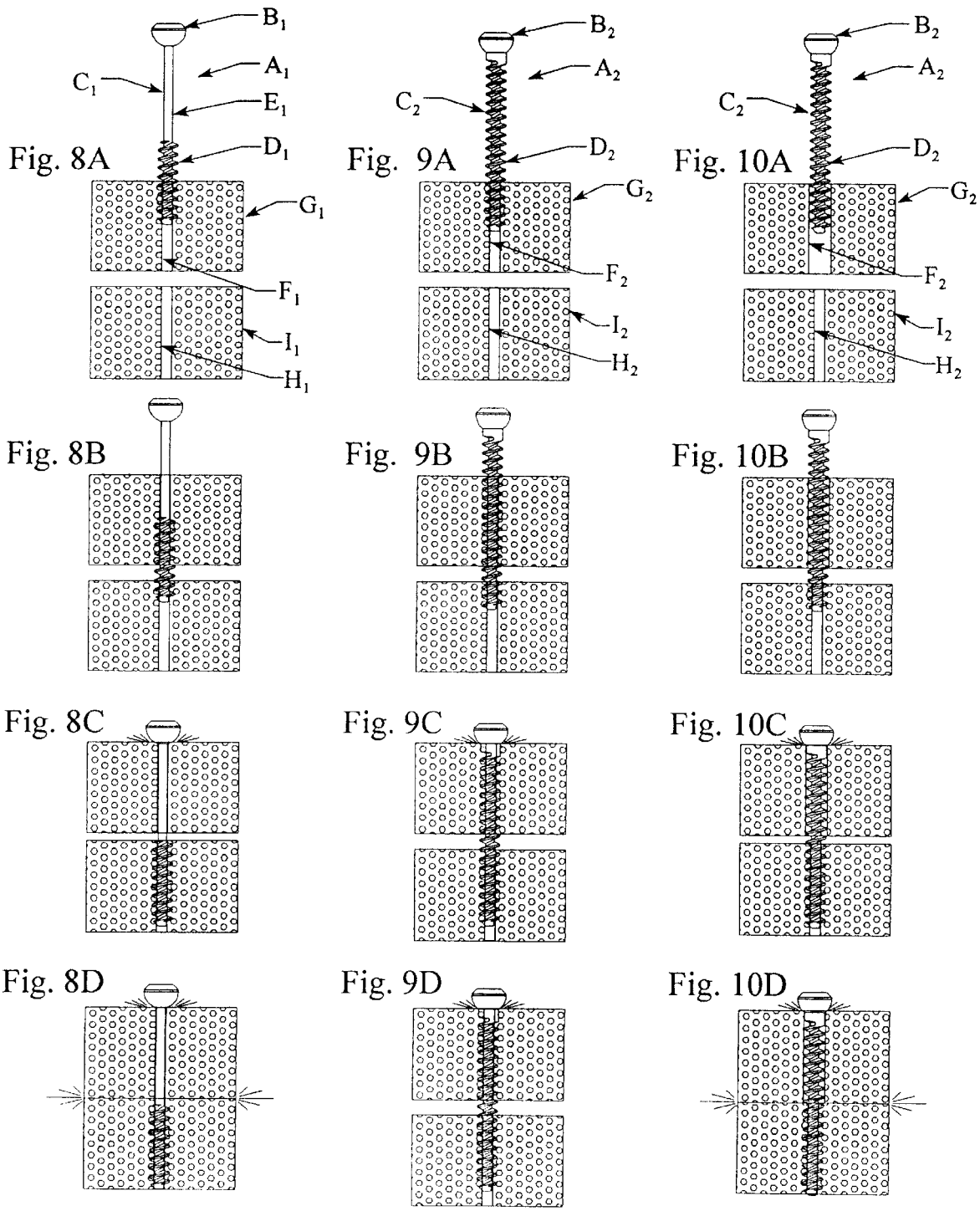

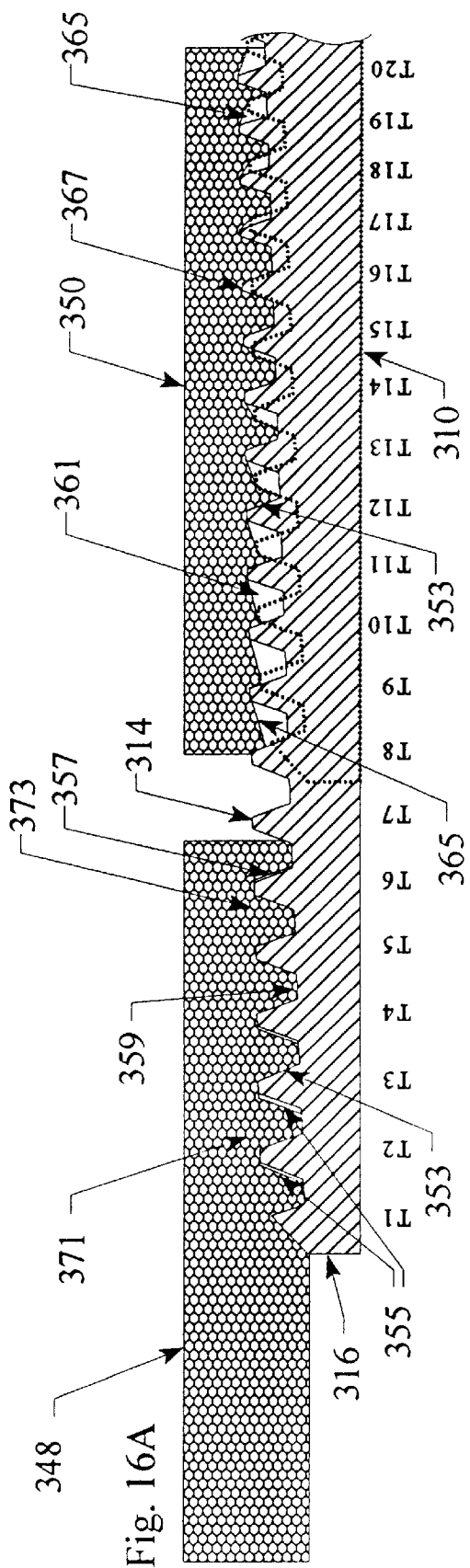
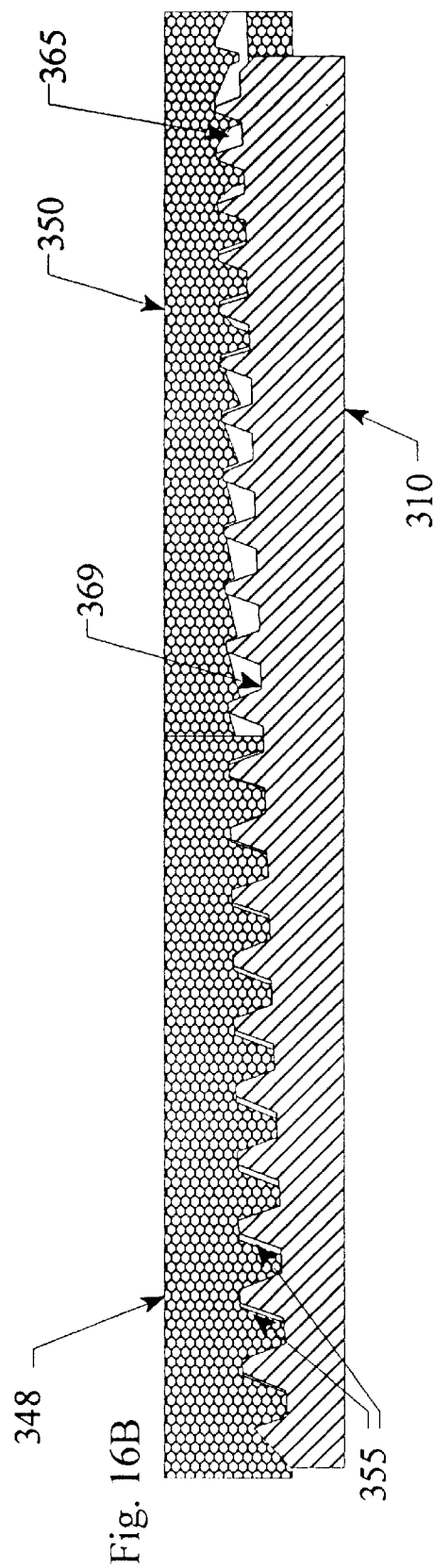
Fig. 16A
Fig. 16B

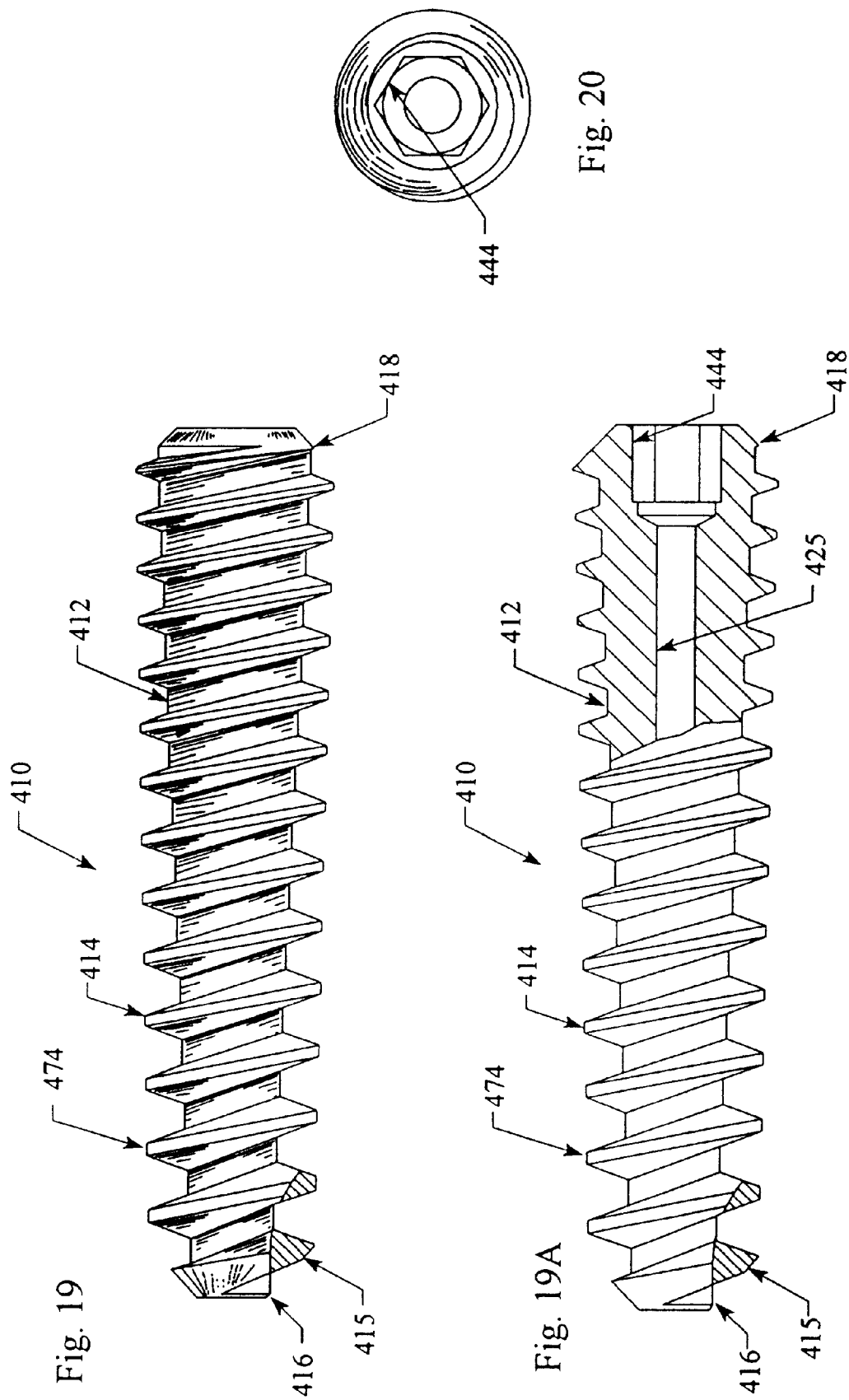

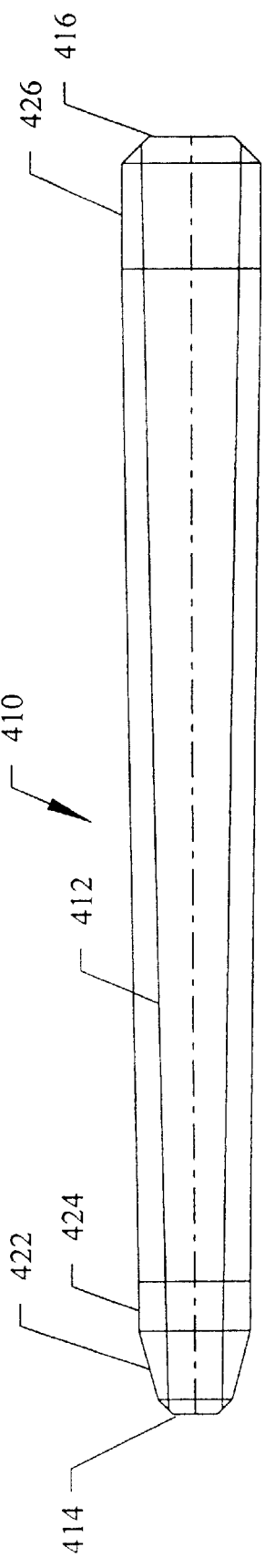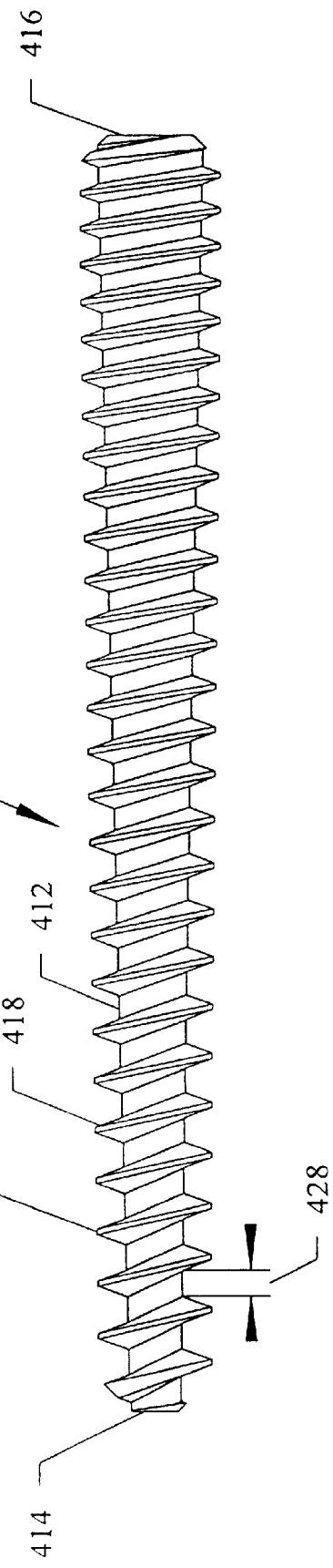

5,964,768

TAPERED BONE SCREW WITH CONTINUOUSLY VARYING PITCH

CROSS-REFERENCE TO RELATED APPLICATIONS

This application is a continuation-in-part of U.S. patent application Ser. No. 08/781,571 filed Jan. 10, 1997, which is a continuation-in-part of U.S. patent application Ser. No. 08/506,469 filed Jul. 25, 1995, which is a continuation-in-part of U.S. patent application Ser. No. 08/332,445 filed Oct. 31, 1994, now U.S. Pat. No. 5,562,672 issued Oct. 8, 1996, which is a continuation of U.S. patent application Ser. No. 08/007,196, filed Jan. 21, 1993. U.S. patent application Ser. No. 08/506,469 is also a continuation-in-part of PCT Application Number PCT/US94/00738, filed Jan. 19, 1994, which claims priority from U.S. patent application Ser. No. 08/007, 196, filed Jan. 21, 1993.

FIELD OF THE INVENTION

The present invention relates generally to a bone screw for drawing together bone fragments separated by a fracture and more particularly to such a screw which draws the bone fragments together as a result of different-pitched threads on the screw.

BACKGROUND OF THE INVENTION

In healing bone fractures it is desirable to compress the fractures so that the fractured surfaces are pressed against one another. In the prior art, bone screws have been used to draw the fractured surfaces together and thereby optimize the healing process.

A number of prior art bone screws have been constructed in a fashion resembling wood screws. For example, some prior art bone screws include a threaded distal portion and a head with a relatively long unthreaded shank disposed between the head and the distal portion. A drill is used to create a bore through the fracture and the screw is threaded into the remote bone fragment with the head of the screw compressing the near fragment tightly against the remote bone fragment.

Other bone screws are threaded along the length thereof, thus requiring a first drill bit to create a bore in both bone fragments extending across the fracture and a second bit to drill a larger bore in the near bone fragment so that the screw threads do not engage the near bone fragment. Thereafter, the screw is tightened in the same manner as described above in connection with the screw having an unthreaded shank, thereby compressing the fragments together.

The operation of two prior art headed lag screws is illustrated in FIGS. 8A–10D. The operation of a lag screw $A_1$ with a head $B_1$ and a shank $C_1$ is shown in FIGS. 8A–D. Shank $C_1$ of screw $A_1$ includes threads $D_1$ at the distal end and an unthreaded region $E_1$ proximal to head $B_1$. The pitch of threads $D_1$ is constant. FIG. 8A shows screw $A_1$ partially engaged in a bore $F_1$ in a near bone fragment $G_1$. The diameter of bore $F_1$ is less than the diameter of threads $D_1$ and therefore the threads engage the walls of the bore as the screw is twisted in. FIG. 8B shows screw $A_1$ as it starts threading into a bore $H_1$ in a remote bone fragment $I_1$. At this point threads $D_1$ are engaged in both bores and moving forward at the same speed in both fragments so no compression between the fragments is achieved. Head $B_1$ has reached the top of fragment $G_1$ in FIG. 8C, as indicated schematically by the radiating "force" lines. Since threads $D_1$ are no longer engaged in fragment $G_1$, screw $A_1$ rotates freely in the fragment without being drawn forward therein. Subsequent rotation of screw $A_1$ draws fragment $I_1$ further up the screw. Because head $B_1$ prevents fragment $G_1$ from moving further up screw $A_1$, fragment $I_1$ is drawn up against fragment $G_1$ and compression between the fragments is achieved as shown in FIG. 8D, with the head pulling down on the near fragment and the threads pulling up on the remote fragment.

The importance of the unthreaded region of screw $A_1$ is illustrated in FIGS. 9A–d. A lag screw $A_2$ including a head $B_2$ and a shank $C_2$ is shown partially engaged in a bore $F_2$ in a near fragment $G_2$ in FIG. 9A. Shank $C_2$ includes threads $D_2$ running the entire length with no unthreaded region such as $E_1$ on screw $A_1$. Rotating screw $A_2$ causes it to be drawn through fragment $G_2$ and pass into a bore $H_2$ in a remote fragment $I_2$ as shown in FIG. 9B. Further rotation of screw $A_2$ brings head $B_2$ down against the upper surface of fragment $G_2$. See FIG. 9C. At this point, threads $D_2$ are still engaged in bore $F_2$ of fragment $G_2$ and the interaction of the head on the surface of fragment $G_2$ impedes the further rotation of screw $A_2$. To have additional rotation, head $B_2$ would have to be drawn down into fragment $G_2$ or the portion of threads $D_2$ in fragment $G_2$ would have to strip out. Therefore a fully threaded screw, such as screw $A_2$, would not be preferred for use in the fragment and bore configuration of FIGS. 9A–D.

The proper bore configuration for using screw $A_2$ is illustrated in FIGS. 10A–D. As shown in FIG. 10A, bore $F_2$ in fragment $G_2$ is enlarged to allow threads $D_2$ of screw $A_2$ to pass freely through the bore. Screw $A_2$ therefore slips into bore $F_2$ until it reaches fragment $I_2$. At that point, threads $D_2$ engage the walls of bore $H_2$ and draw screw $A_2$ down into fragment $I_2$. See FIGS. 10B–C. When head $B_2$ reaches the upper surface of fragment $G_2$, further rotation causes fragment $I_2$ to be drawn up into contact with fragment $G_2$ as shown in FIGS. 10C–D. No binding occurs between head $B_2$ and threads $D_2$ in the near fragment because of the large bore in fragment $G_2$, and the screw functions as intended to draw the two fragments together.

FIGS. 11A–12D illustrate the effect of substituting headless screws in the place of lag screws $A_1$ and $A_2$. FIG. 11A, in particular, shows a headless screw $A_3$ partially installed in a bore $F_3$ in a near fragment $G_3$. Screw $A_3$ includes threads $D_3$ extending along its entire length. The pitch of threads $D_3$ is constant. FIG. 11B shows screw $A_3$ extending through fragment $G_3$ and just entering a bore $H_3$ in a remote fragment $I_3$. FIG. 11C shows screw $A_3$ advanced further into fragment $I_3$. It should be noted that, since the pitch of threads $D_3$ is constant, screw $A_3$ moves forward in fragments $G_3$ and $I_3$ by the same amount with each rotation. As shown in FIG. 11D, screw $A_3$ will pass through both fragments without altering their relative spacing or compressing them together. Thus, a headless screw such as screw $A_3$ will not work to draw the fragments together in the same way as lag screws $A_1$ and $A_2$.

A variation of screw $A_3$ is shown at $A_4$ in FIG. 12A. Screw $A_4$ includes threads $D_4$ of constant pitch extending along its entire length and differs from screw $A_3$ in that it tapers from a smaller outside diameter at the leading end to a larger outside diameter at the trailing end. Screw $A_4$ is shown because it incorporates tapering, which is one of the features of the present invention, however, it is unknown whether such a screw is found in the prior art. Screw $A_4$ is shown partially installed in a bore $F_4$ in a near fragment $G_4$ in FIG. 12A. As screw $A_4$ is rotated, it moves through fragment $G_4$ and into a bore $H_4$ in a remote fragment $I_4$, as shown in FIG. 12B. Subsequent rotation simply carries screw $A_4$ further into and through fragment $I_4$ without any effect on the spacing between the fragments. See FIGS. 12C–D. With a constant pitch thread, such as found on thread $D_4$, the taper does not facilitate compression. Taper may, however, make a screw easier to start in a small pilot hole or even without a pilot hole. The threaded portion of many wood screws follows this general format, tapering to a sharp point, to allow installation without a pilot hole.

It can be seen from the above discussion that a headless screw of constant pitch does not achieve the desired compressive effect between the two fragments as will a lag screw with a head. It is, however, possible to draw two fragments together with a headless screw if it has varying pitch. FIG. 13A shows a headless screw $A_5$ with threads $D_5$ formed along its entire length. Such a screw is shown in U.S. Pat. No. 146,023 to Russell. The pitch of threads $D_5$ varies from a maximum at the leading end to a minimum at the trailing end. It is expected that such a screw moves forward upon rotation in a fragment according to the approximate average pitch of the threads engaged in the fragment. Screw $A_5$ is shown in FIG. 13A with the leading threads engaged in a bore $F_5$ in a near fragment $G_5$. Rotation of screw $A_5$ causes it to move forward into and through fragment $G_5$ and into a bore $H_5$ in a remote fragment $I_5$, as shown in FIG. 13B. Additional rotation after the leading threads engage fragment $I_5$ causes the two fragments to be drawn together. See FIGS. 13C–D. This is because the average pitch of the threads in fragment $I_5$ is greater than the average pitch of threads in fragment $G_5$. Since the screw moves forward in each fragment with each 360° rotation by an amount roughly equal to the average pitch of the threads in that fragment, each rotation will move the screw forward further in fragment $I_5$ than in fragment $G_5$. This effect will gradually draw the fragments together as the screw moves forward. Depending on the initial spacing between the fragments, they can make contact either before or after the trailing end of the screw has entered fragment $G_5$. It should be noted that screw $A_5$, in contrast to constant pitch screws such as screws $A_1$ and $A_2$, can be used to separate fragments $G_5$ and $I_5$ by simply reversing the rotation.

One drawback of a screw such as shown in Russell is the stripping or reaming of the female threads created in the bore by the leading threads as the trailing threads follow. Because the pitch changes along the length of the screw, no thread exactly follows the thread directly in front of it. Rather, each thread tends to cut its own new path which only partially overlaps the path of the thread ahead of it. Thus, the trailing threads tend to ream out the female threads in the bore made by the leading threads. This effect reduces the grip of the trailing threads and therefore the overall compressive force available to urge the fragments together.

FIG. 14A shows a headless screw $A_6$, such as disclosed in U.S. Pat. No. 4,175,555 to Herbert, that offers one solution to the problem of reaming of threads. As noted in the Herbert patent, bone screws having heads suffer from several disadvantages including concentrated loads beneath the screw head and the protrusion of the screw head itself after the screw is installed. Several other shortcomings of the standard type of bone screw are detailed in the Herbert patent.

Screw $A_6$, as per Herbert, includes a shank $C_6$ with leading threads $J_6$ at the leading end, trailing threads $K_6$ at the trailing end and an unthreaded region $E_6$ separating the leading and trailing threads. Threads $J_6$ and $K_6$ each have fixed pitch, but leading threads $J_6$ have a larger pitch and smaller outside diameter than trailing threads $K_6$. FIG. 14A shows leading threads $J_6$ of screw $A_6$ installed in a bore $F_6$ of a near fragment $G_6$. It should be noted that threads $J_6$ do not engage the walls of bore $F_6$, the bore having been bored large enough to allow leading threads $J_6$ to pass freely. As the screw moves forward, the leading threads engage a bore $H_6$ in a remote fragment $I_6$. See FIG. 14B. The diameter of bore $H_6$ is adapted so that leading threads $J_6$ engage the walls. Meanwhile, at the trailing end of the screw, trailing threads $K_6$ start to engage the walls of bore $F_6$, which has been bored to an appropriate diameter therefor.

As soon as trailing threads $K_6$ are engaged in bore $F_6$ and leading threads $J_6$ are engaged in bore $H_6$, the two fragments start drawing together. See FIG. 14C. Further rotation of screw $A_6$ completes the process of moving the two fragments together as shown in FIG. 14D. Screw $A_6$ operates on the same general principle as screw $A_5$, except that the average pitch of the threads in the remote and near fragments is simply the pitch of the leading and trailing threads, respectively. For instance, if the pitch of the leading threads is 0.2 inches and the pitch of the trailing threads is 0.1 inches, each rotation of screw $A_6$ will move it 0.2 inches further into fragment $H_6$, but only 0.1 inches further into fragment $I_6$, thus moving the fragments 0.1 inches closer together.

The Herbert screw overcomes at least one of the drawbacks of the Russell screw, the reaming of female threads by subsequent threads on the screw, but at the same time suffers from a number of other disadvantages. In the Herbert screw, the leading threads have a smaller diameter than the trailing threads. This is necessary to permit the leading threads to pass through the relatively large bore in the near bone fragment and engage the smaller bore in the remote bone fragment. The larger trailing threads then engage the larger bore in the near bone fragment. As a result of this arrangement, any stripping of the threads cut into the bones during installation of the screw occurs in the remote bone. If the stripping occurred in the bore in the near bone fragment, a screw having a head thereon could still be used to compress the fracture even though the near bore was stripped; however, when stripping occurs in the bore in the remote bone, a standard screw with the head thereon cannot be used and another bore must be drilled.

Further, the Herbert screw must be correctly positioned, i.e., it is imperative that the fracture intersect the unthreaded central portion of the Herbert bone screw when the same is installed. Thus, the Herbert screw is not suitable for treating fractures that are very near the surface of the bone where the hole is to be drilled. In addition, because the Herbert screw is not threaded entirely along the length thereof, the purchase obtained by the screw in the bone is not as good as with a screw threaded along the entire length. Also, two bores of different sizes must be drilled to install the Herbert screw rather than a single bore.

Yet another problem with the Herbert screw is the stripping that can occur if additional tightening occurs after the screw has drawn the bone fragments together. While the bone fragments are being drawn together, trailing threads $K_6$ all follow a single path through the near fragment. Similarly, leading threads $J_6$ all follow a single path through the remote fragment. When, however, the bone fragments make contact the two sets of threads can no longer move independently. Further rotation of the Herbert screw after contact between the fragments can cause the leading threads to strip out as they attempt to move forward through the distal bone fragment faster than the trailing threads will allow. See *The Herbert Bone Screw and Its Applications in Foot Surgery, The Journal of Foot and Ankle Surgery*, No. 33, Vol. 4., 1994, pages 346–354 at page 346, which reports on a study that found compression of 10 kg. after only two complete turns of the trailing threads engaged in the near bone fragment. Each subsequent revolution lead to a decrease in compressive force. Thus, care must be taken not to over-tighten the Herbert screw.

In addition to drawing two bone fragments together to repair fractures, it is sometimes desirable to draw together two bones for fusing the same together in connection with arthrodesis of the interphalangeal joints. This procedure is sometimes indicated with symptoms of pain or instability in the finger joints. The purpose is to immobilize and draw together adjacent bones across a joint to cause them to fuse together thereby preventing further movement at the joint.

In one prior art procedure for immobilizing the distal interphalangeal joint (DIP), axial bores are drilled in the articular surfaces of the distal and proximal phalanges. The bore in the distal bone is sufficiently large to receive without threading a screw which is inserted therein via an incision in the tip of the finger. The screw threadably engages the bore in the proximal bone and when the screw head is tightened against the distal end of the distal bone, the two bones are compressed together. After several weeks, the bones fuse together. A second procedure to remove the screw must be performed because the head of the screw will cause discomfort in the finger pad if the screw is not removed.

This procedure is undesirable because it requires two separate surgeries. Katzman, et al., *Use of a Herbert Screw for Interphalangeal Joint Arthrodesis, Clinical Orthopedics and Related Research*, No. 296 pages 127–132 November 1993), describes use of the screw disclosed in the Herbert patent in procedures for interphalangeal joint arthrodesis.

Many of the above-discussed disadvantages associated with using a Herbert screw to compress a fracture are also present when the Herbert screw is used for interphalangeal joint arthrodesis.

It would be desirable to provide a headless bone screw which overcomes the disadvantages associated with the Herbert bone screw, as well as other prior art bone screws.

SUMMARY OF THE INVENTION

A bone screw for drawing together bone fragments separated by a fracture includes a root portion having a leading end and a trailing end. The leading end has a smaller diameter than the trailing end. A screw thread is formed on the root portion between the leading and trailing ends and has a pitch which varies along the length thereof, having a larger pitch near the leading end and a smaller pitch near the trailing end. The thread is adapted to thread in the cancellous material of the respective bone fragments to be joined by the screw. Means are provided on the trailing end of the root portion to accommodate a tool for driving the screw. The present invention also contemplates a method for drawing together bone fragments separated by a fracture.

The foregoing and other objects, features and advantages of the invention will become more readily apparent from the following detailed description of a preferred embodiment which proceeds with reference to the drawings.

BRIEF DESCRIPTION OF THE DRAWINGS

FIG. 1 is an enlarged side elevation view of a bone screw constructed in accordance with the present invention;

FIG. 1A is a view of the screw of FIG. 1 shown partially in cross section;

FIG. 2 is an end view of the bone screw of FIG. 1;

FIG. 3 is a drawing illustrating the outside diameter of the screw;

FIG. 4 is a drawing illustrating the diameter of the root portion of the screw;

FIGS. 8A–14D show the operation of various prior art screws to compress two bone fragments together;

FIGS. 16A–B are detailed views of the screw shown in FIGS. 15C and 15D, respectively;

FIG. 19 is an enlarged side elevation view of a bone screw constructed in accordance with an alternative embodiment of the present invention;

FIG. 19A is a view of the screw of FIG. 19 shown partially in cross section;

FIG. 20 is an end view of the bone screw of FIG. 19;

FIG. 21a illustrates the outside diameter and root profile of an alternative embodiment of the present invention; and FIG. 21b is an elevational view of the screw of FIG. 21a.

DETAILED DESCRIPTION OF THE PREFERRED EMBODIMENT

Figure 5:
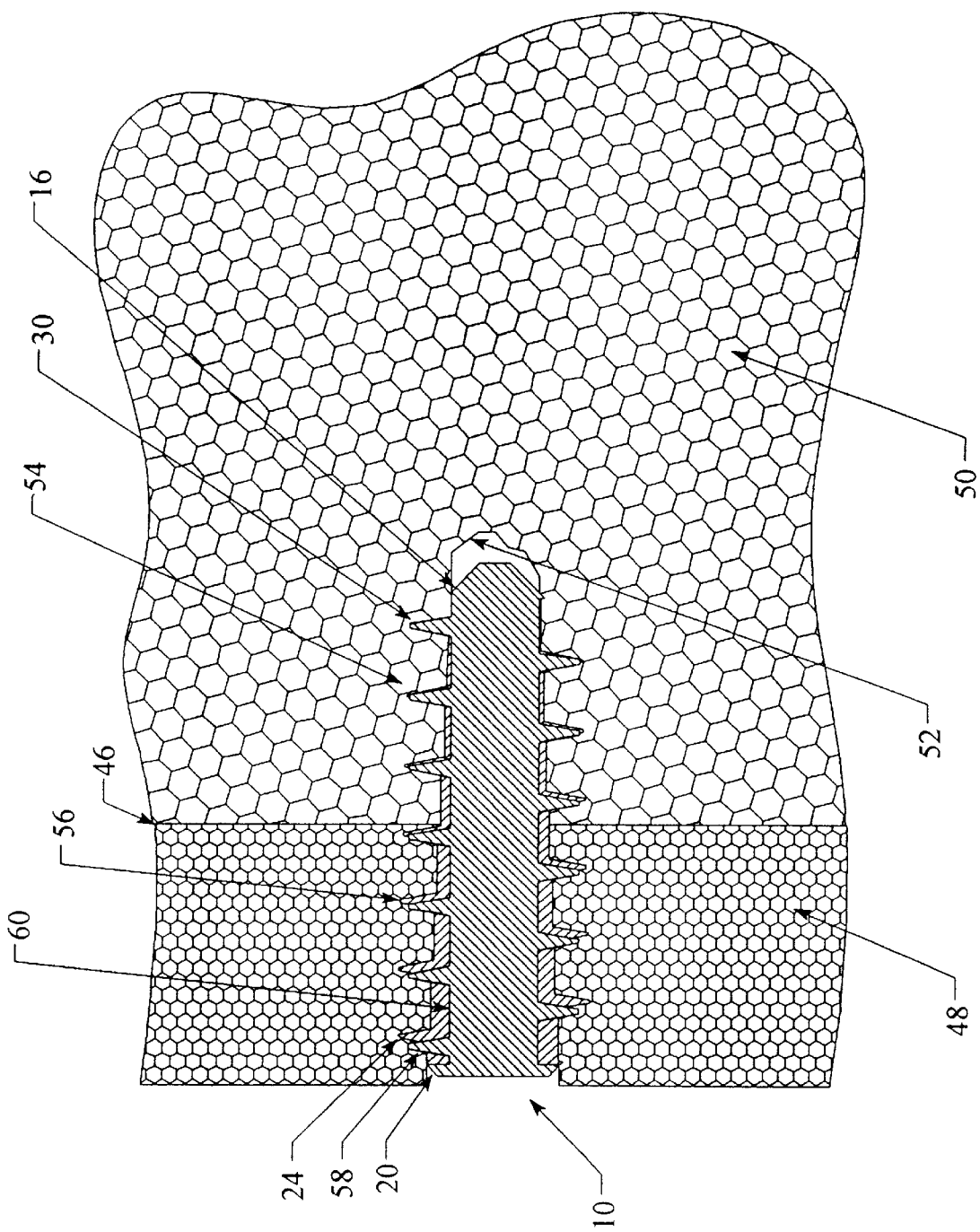
FIG. 5 is a cross-sectional view of a bone screw constructed in accordance with the present invention installed in a bone to draw a fracture together.

Indicated generally at 10 in FIGS. 1 and 1A is a bone screw constructed in accordance with the present invention. Bone screw 10 is centered on a longitudinal axis 11. The length of screw 10 as measured along axis 11 is 0.394 inches in the present embodiment of the invention. The bone screw includes a root portion 12 having a continuous screw thread 14 formed thereon.

Root portion 12 includes a leading end 16 and a trailing end 18. As can best be seen in FIG. 4, the diameter of leading end 16 is less than the diameter of trailing end 18. Also in FIG. 4, it can be seen that root portion 12 tapers between trailing end 18 and leading end 16. A 45° bevel 20, in FIGS. 1 and 1A, is formed on trailing end 18. In the present embodiment of the invention, trailing end 18 has a diameter of approximately 0.092 inches. A frusto-conical nose portion 22 is formed on leading end 16 of root portion 12.

Screw thread 14 extends continuously between nose portion 22 and bevel 20. As can be seen in FIGS. 2 and 3, a trailing thread 24 has a crest height, i.e., the distance between axis 11 and a crest 26 of trailing thread 24, which varies so as to form a substantially 45° angle, illustrated as angle 28 in FIG. 3, between the outside diameter of crest 24 and axis 11.

A similarly tapering leading thread 30 also has a crest 32 which varies in height over a first partial turn of screw thread 14 so as to form an angle of substantially 45° with axis 11 as illustrated in FIG. 3.

The crest of screw thread 14 between trailing and leading threads 24, 30 respectively, varies in height along the length of thread 14. In the present embodiment of the invention, the outside diameter defined by the crest of thread 14 between the leading and trailing threads forms an angle 34, in FIG. 3, of approximately 1.43° with respect to an axis 35 extending from the radially outermost portion of thread 14 parallel to axis 11. In the present embodiment of the invention, the diameter of the radially outermost portion of thread 14 is approximately 0.138 inches.

The pitch of thread 14, i.e., the distance from one point on the thread to the corresponding point on an adjacent thread measured parallel to axis 11, decreases between the leading and trailing ends of the screw. It should be noted that the term pitch is also sometimes used to refer to the number of threads per unit length, i.e., 20 threads per inch. This alternative definition is simply the inverse of the definition chosen for use in this application. The distinction is important to remember for proper understanding of the subsequent description because the screw of the present invention relies on varying pitch to achieve its function.

In the embodiment of the invention shown in FIGS. 1 and 1A, the distance between the uppermost portion of crest 32 and a corresponding crest portion 36 is 0.04964 inches. The distance between the uppermost portion of crest 26 and a corresponding crest portion 38 is 0.04748 inches. In the present embodiment of the invention, the pitch change per revolution is approximately 0.00036 inches.

The pitch depth, i.e., the distance between the crest and the radially outer surface of root portion 12 similarly varies along the length of the screw. In the present embodiment of the invention, the pitch depth where leading thread 30 joins the remainder of screw thread 14 is approximately 0.0302 inches. The pitch depth where trailing thread 24 joins the remainder of thread 14 is approximately 0.0240 inches.

The decrease in pitch depth between the leading end and trailing end of the screw can be seen by comparing FIG. 3 and FIG. 4 wherein root portion 12 tapers more sharply from the trailing to the leading end of the screw than does the change in crest height as shown in FIG. 3. In the present embodiment of the invention, the outside diameter of root portion 12 between leading and trailing ends, 16, 18, respectively, forms an angle 40, in FIG. 4, of approximately 2.5° with respect to an axis 42 extending from the radially outermost portion of trailing end 18 parallel to axis 11.

A hex socket 44 is formed on the trailing end of screw 10 to accommodate a driver as will be hereinafter further explained in connection with a description of the procedure in which the screw is used to draw opposing fragments of a fractured bone together.

An alternative embodiment of the screw of the present invention is shown generally at 410 in FIGS. 19 and 19A. Screw 410 includes a root portion 412 on which is formed a thread 414. Thread 414 extends from a leading end 416 to a trailing end 418 and includes a land 474. The pitch of thread 414 at the leading end is 0.055 inches and the pitch at the trailing end is 0.035 inches. The land varies from 0.010 inches to 0.004 inches overt the same range. Thread 414 includes a cutting flute 415 near the leading end to facilitate the cutting of female threads as the screw is installed. Both the outside diameter of thread 414 and root 412 taper from a smaller value at the leading end to a larger value at the trailing end. See FIGS. 21–22. The root diameter tapers from 0.062 inches to 0.122 inches, while the outside diameter tapers from 0.130 inches to 0.156 inches. The length of screw 410 is 0.689 inches.

Screw 410 also includes an axial bore 425 which extends from the leading end to the trailing end. Bore 425 is adapted to receive a stiff guide wire, not shown, which facilitates installation of screw 410. A hex socket 444 is formed at the trailing end to allow the screw to be driven by an hex wrench. See FIG. 20.

Turning now to FIG. 5, illustrated therein is a fracture 46 which separates adjacent bone fragments 48, 50. Screw 10 is illustrated installed in a bore 52 which extends through bone fragments 48, 50 across fracture 46.

In installing screw 10, a surgeon first drills bore 52 across bone fragments 48, 50 as shown. The bit may be a conventional cylindrical bone bit or may comprise a bit having a slight taper from the leading to the trailing end thereof. Thereafter, the surgeon inserts a tool (not shown) having a hex driver extending therefrom which is connectable to hex socket 44 for screwing screw 10 into bore 52. Bore 52 is of a size to just receive leading end 16 of screw 10. As soon as nose portion 22 is received within the bore, torque is applied using the tool inserted into hex socket 44 thereby causing leading thread 30 to cut into the bone adjacent bore 52.

In the view of FIG. 5, screw 10 is hatched to show the path cut by leading thread 30 after screw 10 is installed in the position illustrated in FIG. 5. The path of thread 30 is depicted using hatching, like hatching 54, 56, 58 which indicates the position of the path cut by leading thread 30 relative to succeeding threads of the screw. Hatching 60 depicts the actual position of the thread on screw 10 and root 12. It is to be appreciated that hatching 54, 60 are not used in FIG. 5 to depict different structure, which is unitary as illustrated in FIG. 1, but to depict relative positions of the path cut by leading thread 30 in the actual position of subsequent threads in the installed screw.

Because of the decreasing pitch along the length of the screw, each successive thread received in the path cut by thread 30 exerts pressure against the right side (as viewed in FIG. 5) of the path cut by thread 30 thereby tending to compress the bone along the length of the screw. As can be seen in FIG. 5, by the time the screw is fully installed, trailing thread 24 compresses a substantial amount of bone when it is received in the path cut by thread 30. This tends to draw bone fragments 48, 50 tightly together across fracture 46 thereby promoting healing of the fracture.

As can be appreciated from the view of FIG. 5, the thread taper is important for two reasons. First, each succeeding portion of the thread is spaced further radially outwardly as a result of the taper and therefore the outer portion of each thread (that portion closely adjacent the crest) cuts into new bone which was not cut by the preceding thread. This provides a much better purchase than would a thread having a continuously varying pitch with constant diameter. In such a configuration, each succeeding thread cuts additional bone within the generally cylindrical volume defined by the outside diameter of the threads. The outer portion of each thread (that portion closely adjacent the crest) therefore cuts into bone uncut by the preceding thread.

The tapered root is also advantageous in that the radially outer surface of the root, i.e., that portion between adjacent threads, is tightly urged against uncut bone defining the wall of bore 52. It is desirable to maximize the surface area of screw 10 urged against adjacent bone, rather than a space cut by a thread, to increase purchase of the screw.

Figure 15A:
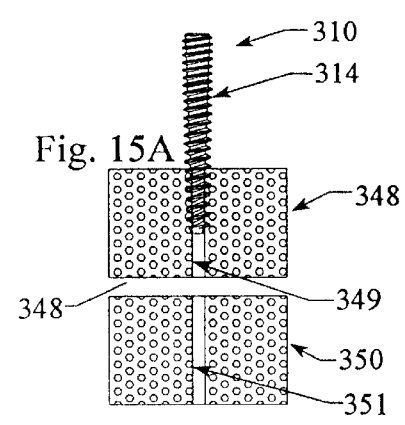
FIGS. 15A–D show the operation of a screw constructed according to an alternative embodiment of the present invention to compress two bone fragments together.
Figure 13B:
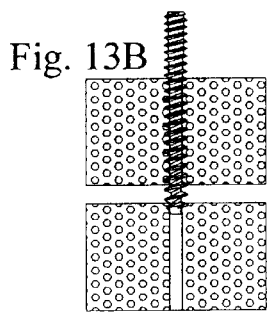
Figure 14B:
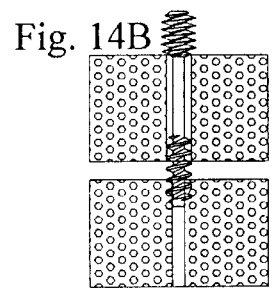
Figure 15B:
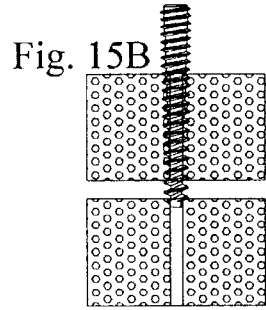
Figure 13C:
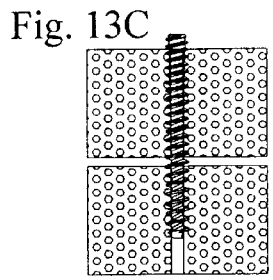
Figure 14C:
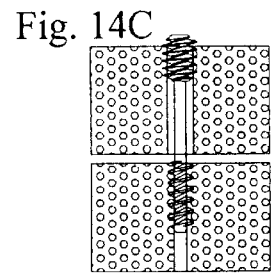
Figure 15C:
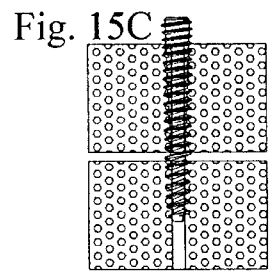
Figure 13D:
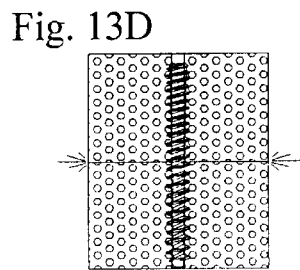
Figure 14D:
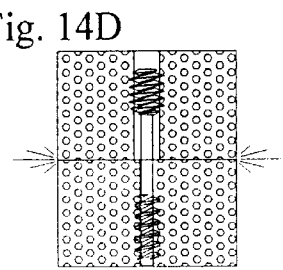
Figure 15D:
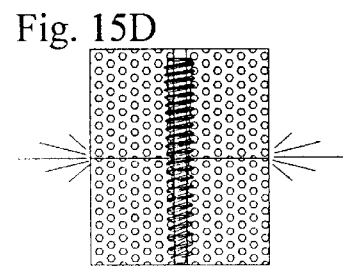

The details of the operation of the screw of the present invention, as currently understood, may be better appreciated by examination of FIGS. 15A–D and FIGS. 16A–B and the following description. FIGS. 15A–D illustrate the operation a screw 310 to draw together and join bone fragments 348 and 350. FIG. 15A shows screw 310 partially installed in a bore 349 in bone fragment 348. Screw 310 is shown just entering a bore 351 in bone fragment 350 in FIG. 15B. Subsequent rotation of screw 310 starts the process of drawing the bone fragments together as shown in FIGS. 15C–D.

FIG. 16A shows the interaction of a thread 314 in bores 349 and 351 when screw 310 is positioned therein as shown in FIG. 15C. In FIG. 16A a leading end 316 of screw 310 is engaged in bore 349. Each revolution of the thread 314 is labeled for reference in the subsequent discussion, from thread T1 at the leading end to thread T23 at the trailing end.

As the screw moves through bone fragments 348 and 350, thread 314 will cut a mating female thread 353. However, because the pitch of thread 314 changes along the length of the screw, female thread 353 will not precisely match thread 314 of screw 310 along its entire length. In particular, since subsequent threads will not track in the same path as the preceding threads, a pattern of leading gaps 355 and trailing gaps 357 will evolve between female thread 353 and screw thread 314 as the screw moves forward in the bores.

The screw will move forward in the bone fragment with rotation at a rate that is a function of the competing forces from all of the threads engaged in the bore. The rate will correspond to an effective pitch of the threads in the bore and will be equal to the pitch of the screw at an effective pitch point 359 along the portion of the screw engaged in the fragment. As more of the screw enters the bore, the effective pitch point will move back along the screw and further into the bone fragment. Once the screw extends completely through the bone fragment, the location of the effective pitch point will stabilize at a relatively constant location in the bone fragment, simply moving back along the screw at the rate the screw moves forward in the bore. The threads ahead of the effective pitch point, which will be referred to as the pulling threads 371, will have greater pitch than the effective pitch. Similarly, the threads behind the effective pitch point, or dragging threads 373, will have a pitch that is smaller than the effective pitch. In FIG. 16A the pulling threads in fragment 348 are $T_1$–$T_4$ and the dragging threads are $T_5$ and $T_6$.

Each rotation of the screw will move it forward in fragment 348 by an amount corresponding to the present value of the effective pitch. In FIG. 16A the effective pitch will be equal to the pitch of thread 314 between threads $T_4$ and $T_5$. Starting at the leading end, thread $T_1$ will always be cutting a new thread path in the fragment, so no gap will form around it. Thread $T_2$, however, will attempt to follow the track of thread $T_1$ in fragment 348, which would carry it forward by an amount equal to the pitch between thread $T_1$ and $T_2$. Since, however, the screw will only move forward by the effective pitch, i.e., the pitch between threads $T_4$ and $T_5$, thread $T_2$ can only move forward by the same amount. This causes thread $T_2$ to pull back against the surrounding bone and creates a leading gap in front of that thread. Similarly, thread $T_3$ will attempt to move into the position of thread $T_2$, but will be held back from moving as far forward as its pitch would indicate, thus creating a leading gap as thread $T_3$ is pulled back against the surrounding bone. Behind the effective pitch point, thread $T_5$ will attempt to move into the prior position of thread $T_5$, but will be dragged forward somewhat, leaving a trailing gap.

The pattern of leading and trailing gaps created by screw 310 in bone fragment 350 is also shown in FIG. 16A. Bone fragment 350 includes leading gaps 361 and trailing gaps 363 similar to those found in bone fragment 348. However, because more of the screw has moved through bone fragment 350, the gaps have evolved to a greater extent. The earlier position of screw 310 in fragment 350 is shown in dotted lines in FIG. 16A to illustrate the evolution of the threads as the screw moves forward.

In the earlier position of screw 310, the effective pitch point falls at approximately thread $T_8$. With the screw positioned as shown, the effective pitch point is at approximately thread $T_{16}$, the screw having completed approximately 8 revolutions between the two positions. The current and prior screw positions are aligned at effective pitch point 367 in fragment 350 based on the assumption that thread 314 will track through this point uniformly. The evolution of the position of threads behind and ahead of the effective pitch point can thus be seen by comparing the prior position with the current position.

Leading gaps 361 have a sloping upper surface 365, which is a result of the gradual expansion of the outside diameter of thread 314 toward the trailing end of the screw. Upper surface 365 represents a line from the prior position of the thread to the position as shown. As thread 314 at a given point in the bone fragment is held back, it simultaneously expands in diameter. This effect prevents thread 314 from completely reaming out the female thread in the bone fragment, as discussed above. Without the taper, sloping upper surface 365 would be flat and as soon as the width of the gap grew to equal the spacing between the threads, there would be no purchase left for subsequent threads along a portion of the bore.

Once the leading end of screw 310 has passed through bone fragment 351 the effective pitch point remains at a relatively constant position along the bore for the remainder of the screw. If the pitch change per revolution is dP and the effective pitch points are separated by N threads, then the bone fragments will be drawn together by a distance N times dP for every revolution of the screw. In screw 310, dP=0.0008 inches and the effective pitch points are separated by approximately 11 threads, therefore the gap between the bone fragments will close by about 0.009 inches per revolution.

It is thought that the effective pitch point will be somewhat behind the geometric middle of the portion of the screw engaged in the bore as shown in FIG. 16A. Because bone becomes less dense near the center in the cancellous portion, the threads nearer to the surface in the cortex are expected to have greater effect. Also, the threads nearer the surface are of larger diameter because of the taper in the outside diameter of the thread.

The other factor tending to cause the pitch point to be closer to the surface of the bone relates to balancing the amount of bone displaced as the leading and trailing gaps are formed. As shown in FIG. 16A, the pulling threads 371, which have pitch greater than the effective pitch, are held back from moving as far forward with each rotation as their pitch would indicate. Likewise, dragging threads 373 are drawn forward faster than their pitch would dictate. This effect creates leading gaps 355 in front of pulling threads 371 as they pull against the surrounding bone. Similarly, trailing gaps 357 form behind dragging threads 373 as they are dragged forward through the surrounding bone.

Since the leading and trailing gaps are formed in opposition to one another, it is reasonable to assume that they will evolve at a relatively balanced rate. Combining this assumption with the fact that the effective pitch point is constantly moving forward in the bone fragment as the screw enters, suggests that the effective pitch point will be behind the geometric middle of the portion of the screw in the bone fragment. Because the effective pitch point is moving forward in the bone fragment by approximately one-half the pitch change per revolution, the dragging threads will be dragged forward by approximately an extra one-half the pitch change per revolution for each revolution of the screw. The fact that the effective pitch point is moving forward means that the pulling threads are not held back as much as would be the case if the effective pitch point remained constant. If the movement of the two thread regions through the bone are balanced, then the effective pitch point will not move forward in the bone fragment as rapidly as would otherwise be expected and the effective pitch point will lie behind the geometric middle.

FIG. 16B shows how the pattern of gaps changes once the two bone fragments have been drawn together. After the bone fragments meet, the pattern of gaps starts to evolve toward that found in a single fragment. In particular, gaps form or increase on the leading side of all of the pulling threads ahead of an effective combined pitch point 369, and on the trailing side of all the dragging threads behind the effective combined pitch point. Near the joint between the fragments, the gaps will generally transition from leading to trailing and vice versa, because the dragging threads in fragment 348 near the joint are converted to pulling threads after the joint closes. The pulling threads in fragment 350 likewise become dragging threads after the fragments meet.

Rotation of screw 310 after the bone fragments have come together tends to increase the pressure in the joint between them. Additional rotation can be used to set the depth of the screw as desired. Since the outside diameter of the thread tapers, as described above, the screw can be driven in until the trailing end is below the surface of the bone without danger of stripping the female thread formed by the preceding threads, even if the bone fragments first meet with the trailing end protruding substantially. This is because subsequent threads expand and cut into some new bone even as they partially ream the female threads left by preceding threads on the screw. This is in contrast to the Herbert screw, where, as discussed above, additional tightening after the fragments have come together can strip out the threads in the distal fragment and reduce compression. Since it is important in the preferred application of the present invention to have the trailing end of the screw below the surface of the bone, this is an important feature and advantage over prior art screws.

The tolerance in the screw of the present invention to further tightening after the fragments have come together is also important because it simplifies the installation process by eliminating the danger of over-tightening that must be guarded against when using the Herbert screw.

Figure 6:
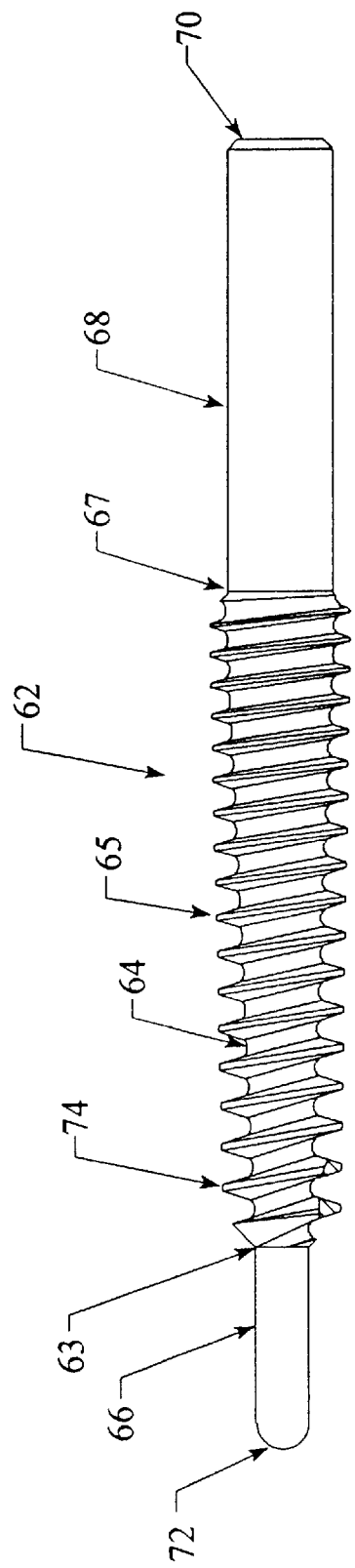
FIG. 6 is a side elevation view of a bone screw constructed in accordance with the present invention which may be used for interphalangeal joint arthrodesis.

Turning now to FIG. 6, indicated generally at 62 is a second embodiment of a bone screw constructed in accordance with the present invention. Bone screw 62 is sized and constructed for use in connection with interphalangeal joint arthrodesis. Screw 62 includes a tapered root 64 having a thread 65 formed thereon from a leading end 63 to a trailing end 67, a substantially cylindrical leading extension 66 joined to the leading end and a substantially cylindrical trailing extension 68 joined to the trailing end. The diameter of leading extension 66 is slightly larger than root 64 at leading end 63, while the diameter of trailing extension 68 is slightly smaller than root 64 at trailing end 67. The trailing extension 68 includes a hex socket (not visible), like hex socket 44 in FIG. 1A, formed on an end surface 70 thereof. Leading extension 66 includes a tapered nose 72 formed on the forward end thereof. In the present embodiment of the invention, screw 62 is 1.259 inches in length with the threaded portion being 0.630 inches long and the diameter of leading extension 66 being 0.05 inches. The trailing extension diameter is 0.100 inches. As is the case with the previously described embodiment, the pitch of thread 65 decreases between the leading and trailing ends. In the embodiment of FIG. 6, a land 74 is formed in the crest of thread 65 and decreases in width between the leading and trailing ends of the screw.

Figure 7:
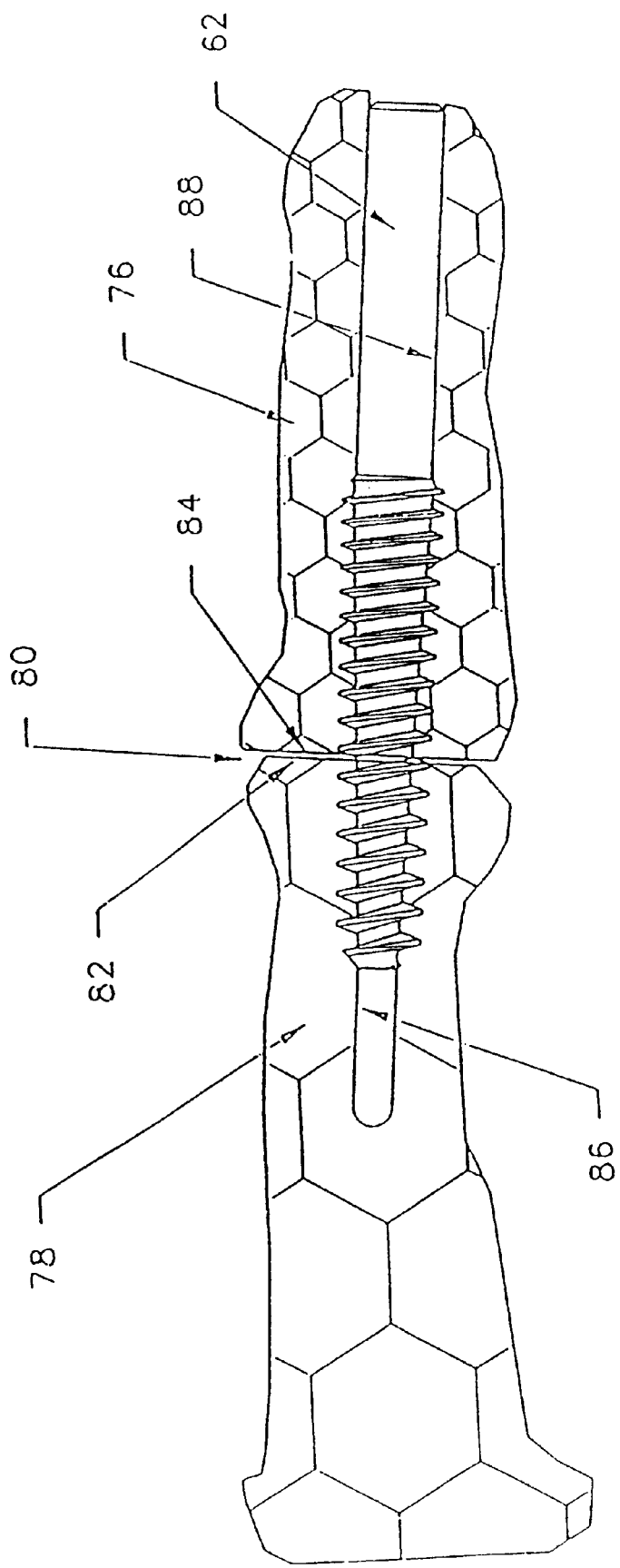
FIG. 7 is a view of the bone screw of FIG. 5 installed in a distal interphalangeal joint with the bones forming the joint as shown in cross-section.
Figure 11A:
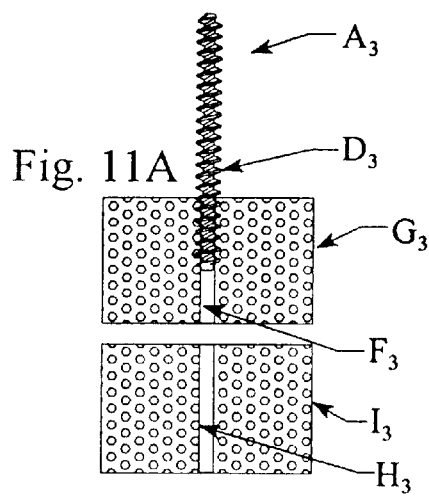
Figure 12A:
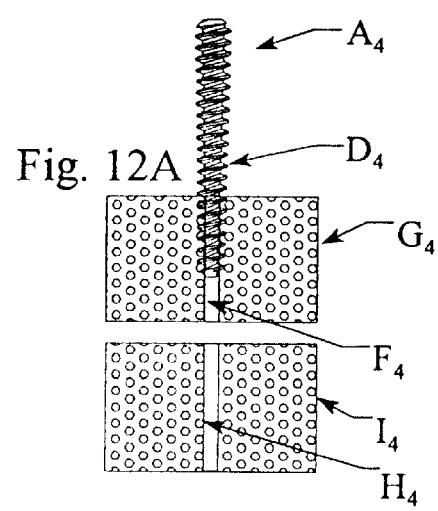
Figure 11B:
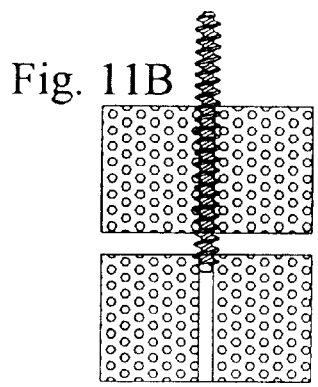
Figure 12B:
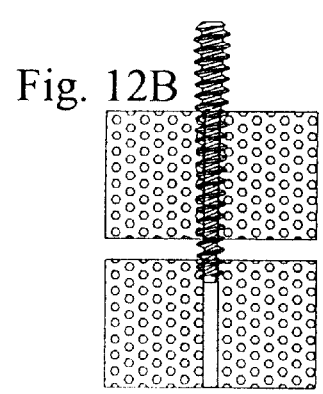
Figure 11C:
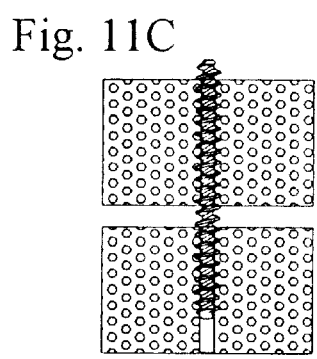
Figure 12C:
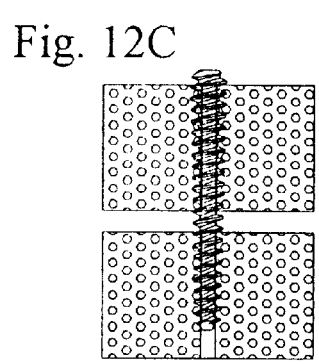
Figure 11D:
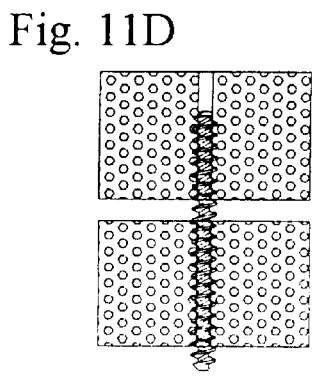
Figure 12D:
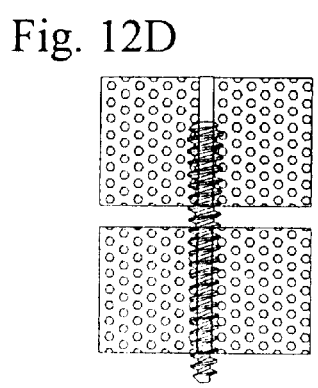
Figure 13A:
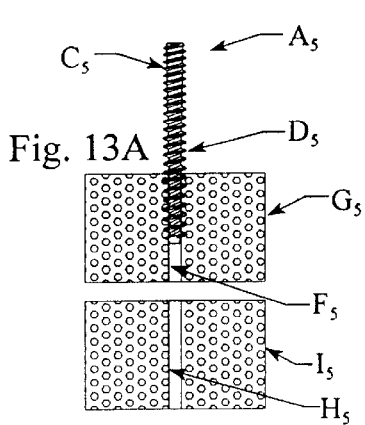
Figure 14A:
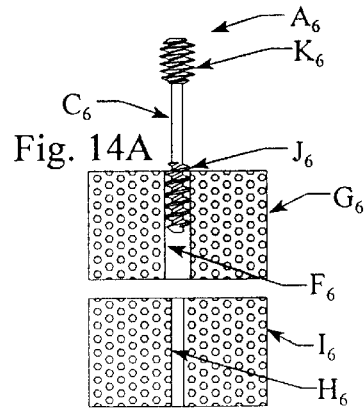

Turning now to FIG. 7, a distal phalanx 76 comprises the outermost bone of one of the four fingers. A proximal phalanx 78 is adjacent thereto with a distal interphalangeal (DIP) joint 80 being formed therebetween.

The joint includes a pair of articular surfaces 82, 84 which have been flattened in accordance with a known technique for immobilizing DIP joint 80. Bores 86, 88 are drilled into each of phalanxes 76, 78 from articular surfaces 82, 84, respectively. Thereafter the bones are repositioned as shown in FIG. 7 and screw 62 is driven into the distal end of the bore in phalanx 76 until the screw is positioned as shown in FIG. 7.

Screw 62 thus compresses across joint 80 even though it has a relatively small diameter, which is critical in DIP joint arthrodesis because of the small diameter of the bones involved. Screw 62 also has sufficient length, due to the leading and trailing extensions 66, 68, to provide stability while the bones are fusing. Because the screw is entirely received within the bones, i.e., there is no protrusion from the screw, it can remain implanted and thus a second procedure to remove the bone is not necessary.

Figure 17A:
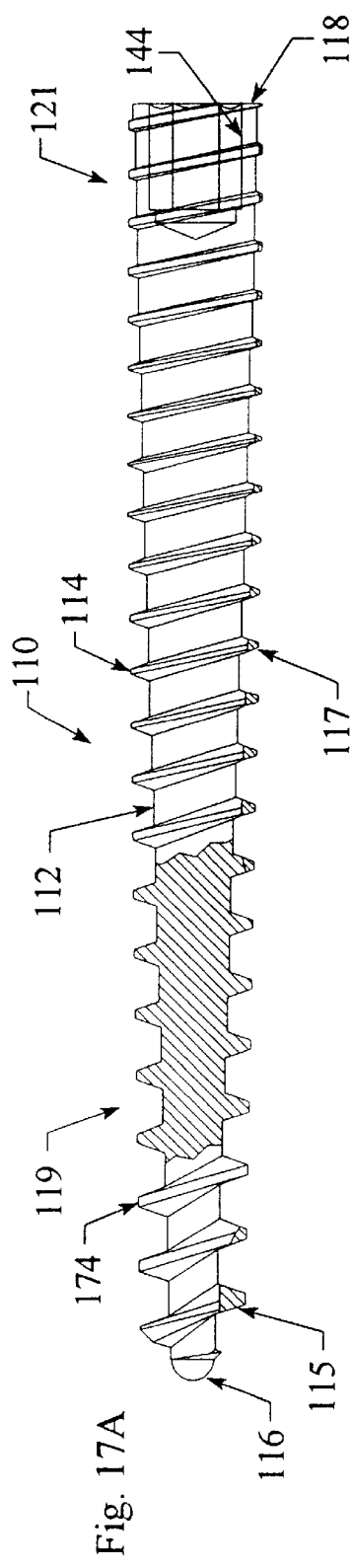
FIG. 17A is a side elevation view of a bone screw constructed according to an alternative embodiment of the present invention.

A third embodiment of a screw constructed according to the present invention is shown generally at 110 in FIG. 17A. Screw 110 includes a root portion 112 on which is formed a continuous screw thread 114 and associated land 174. Screw 110 includes a leading end 116 and a trailing end 118. Leading cutting flutes 115 are formed in thread 114 near leading end 116 to help the thread self tap into the bone. A series of trailing cutting flutes 117 are formed in thread 114 along the sides of the screw toward the trailing end. Trailing cutting flutes 117 facilitate installation and removal of the screw by helping to cut a thread path in the bone. Screw 110 may be formed with two sets of trailing cutting flutes, one oriented to cut female threads upon insertion and another oriented to cut female threads upon removal of the screw, thus easing both installation and extraction. A hex socket 144 is formed in the trailing end of screw 110 to receive a drive tool.

Screw 110 is formed with a variable pitch portion 119 and a constant pitch portion 121. Variable pitch portion 119 extends from leading end 116 back toward trailing end 118 for about 70 percent of the length the of the screw. The length of the screw is 0.961 inches. It should be noted that screw 110 does not include a bevel at the trailing end as formed on screw 10 and shown at 20 in FIG. 1A. The bevel was eliminated in screw 110 to provide additional structural support around hex socket 144 which is used for driving the screw.

Figure 17B:
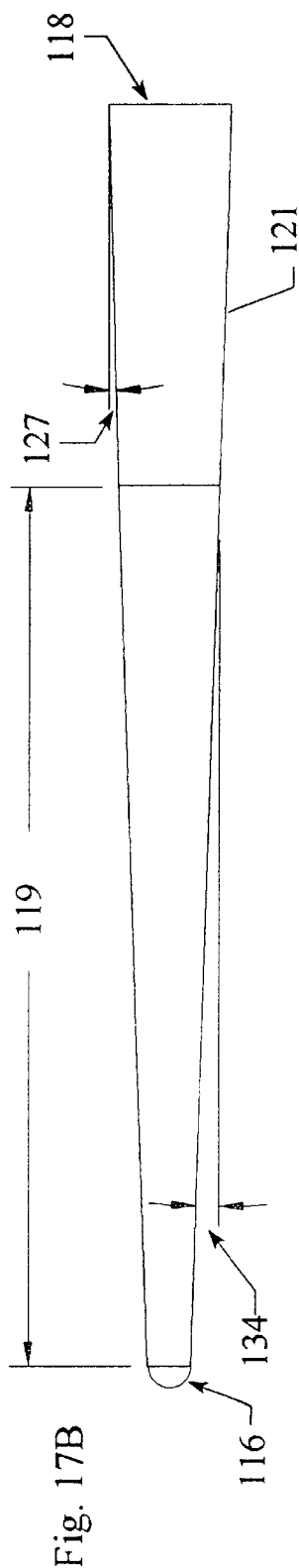
FIG. 17B is a representation of the side profile of a root portion of the screw of FIG. 17A.
Figure 17C:
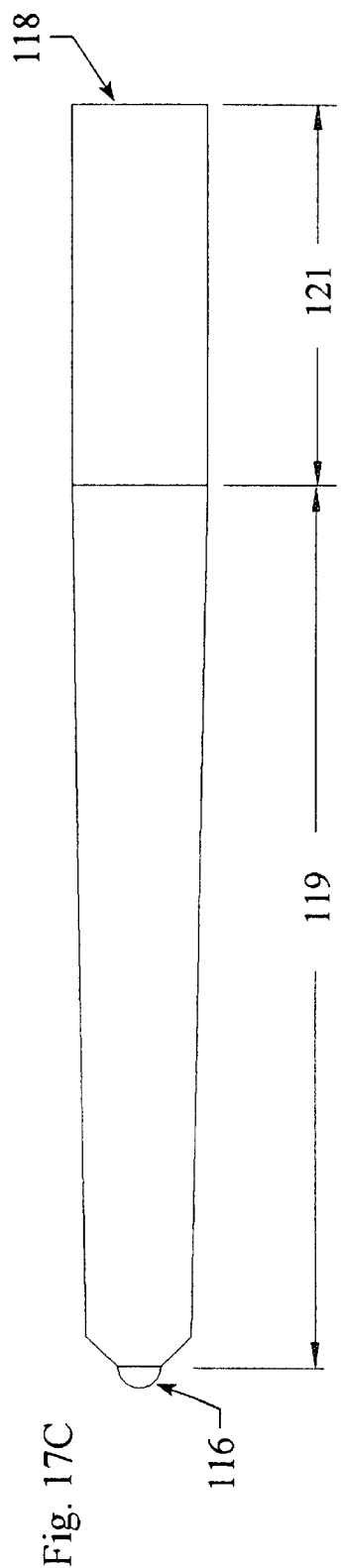
FIG. 17C is a representation of the outside diameter of the screw of FIG. 7A.

Variable pitch portion 119 of screw 110 is formed according to the previously described construction of screw 10. In particular, the pitch of thread 114 is largest at leading end 116 and decreases over variable pitch portion 119 back toward trailing end 118. The pitch starts at 0.050 inches and decreases to 0.0365 inches at the trailing end of the variable pitch portion. As shown in FIG. 17B, root portion 112 tapers outward from leading end toward trailing end over variable pitch portion 119 with an angle 140 of 1.93° relative to the longitudinal axis of the screw. The diameter of the root portion is 0.032 inches at the leading end and 0.091 inches at the trailing end. The outside diameter of thread increases over the same region at an angle 134 of 1.0°. See FIG. 17C. The outside diameter of the thread at the leading end is 0.077 inches and 0.1 inches at the trailing end.

The construction of constant pitch portion 121 is considerably different from that of variable pitch portion 119. The pitch and outside diameter of thread 114 are constant over the section of the screw forming constant pitch portion 121. Root portion 112 continues to taper outward relative to the axis of the screw but at a lesser angle 127 of 1.57° over the constant pitch portion. The width of land 174, i.e., the flat at the crest of the thread, which decreases from the leading end over the variable pitch portion, increases over the length of the constant pitch portion toward the trailing end. Land 174 starts at the leading end at 0.008 inches and decreases to 0.002 inches at the end of the variable pitch region. Land 174 starts to increase again moving back over the constant pitch portion, reaching a value of 0.006–0.007 inches at the trailing end.

The constant pitch portion at the rear of screw 110 allows construction of a longer screw without the commensurate increase in diameter that would occur by extending the structure of the variable pitch portion. This is important where the screw is to be used in small bones that cannot accept a larger bore, but which require a longer screw. A longer screw may be required to reach deeper fractures or for use in fusing two bones together. Screw 110 is particularly suitable for use in distal interphalangeal fusions in the hand as described above.

Figure 18A:
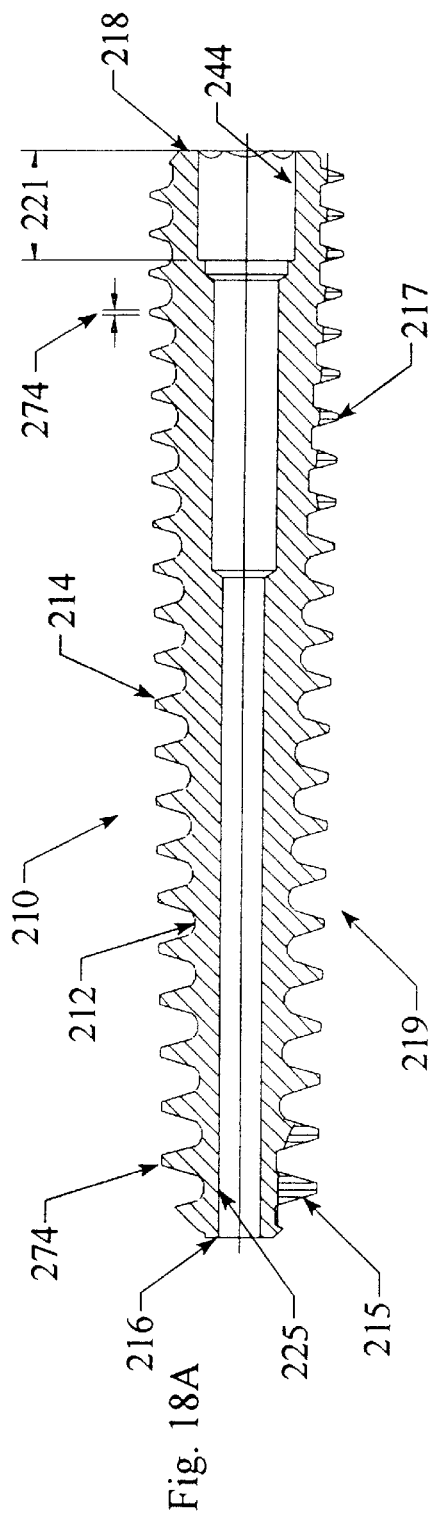
FIG. 18A is a side elevation view of a bone screw constructed according to a fourth embodiment of the present invention.
Figure 18B:
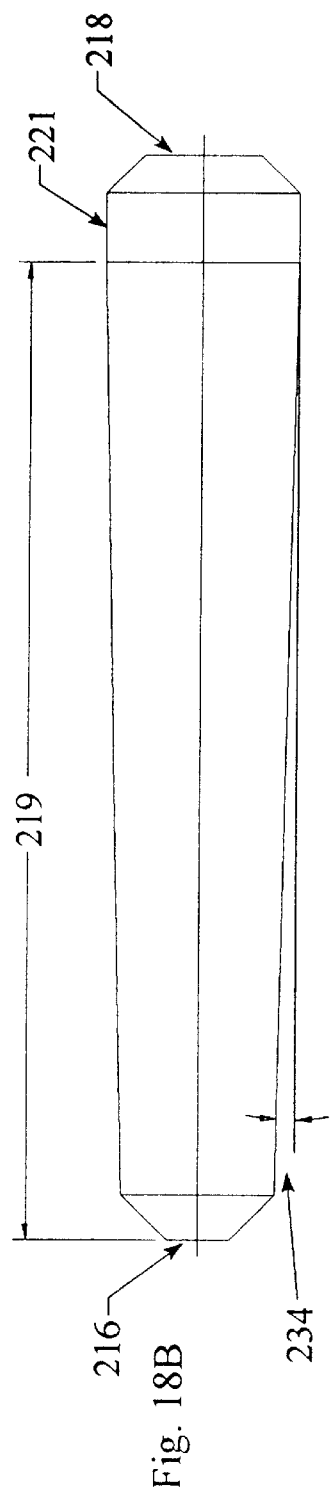
FIG. 18B is a representation of the side profile of a root portion of the screw of FIG. 18A.

A fourth embodiment of a screw constructed according to the present invention is shown at 210 in FIG. 18A. Screw 210 is generally similar to screw 110 of FIG. 17A, and includes a root portion 212, a thread 214, a leading end 216 and a trailing end 218. Screw 210 also includes a variable pitch portion 219 and a constant pitch portion 221. See FIG. 18B. The diameter of root portion 212 tapers at an angle 240 of 2.29° from 0.050 inches at the leading end to 0.106 inches at the trailing end. The outside diameter of thread 214 tapers at an angle 234 of 1.2° from 0.110 inches to 0.140 inches over the same range. The overall length of screw 210 is 0.787 inches.

Figure 18C:
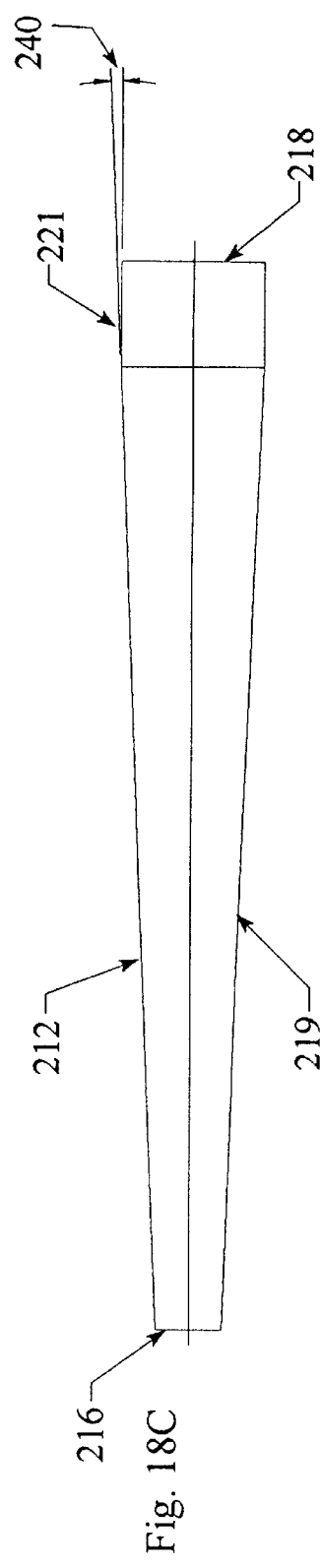
FIG. 18C is a representation of the outside diameter of the screw of FIG. 8A.

The principal difference between screws 110 and 210 is found in the constant pitch portions. In screw 210, neither the root portion nor the outside diameter of the thread is tapered in the constant pitch region. See FIGS. 18B–C. Screw 210 is designed, like screw 110, to have additional length without additional thickness. If additional length is desired, it is possible to form screw 210, or screw 110, with leading and/or trailing extensions such as found on screw 62 in FIG. 6.

Thread 214 on screw 210 includes a land 274. Land 274 starts at a maximum of 0.007 inches at the leading end and decreases to 0.003 inches at the trailing end. In contrast to screw 110, land 274 does not increase over the constant pitch portion. Thread 214 also includes leading cutting flutes 215 and trailing cutting flutes 217 to facilitate installation and removal.

Screw 210 also varies from screw 110 in that it includes an axial bore 225. Axial bore 225 permits screw 210 to be guided into the bone on a stiff wire to facilitate positioning and prevent the screw from wandering off axis as it is driven in.

It should be noted that the length, number of threads, pitch, pitch change per revolution and the various diameters are not critical to the present invention and can be varied without departing from the spirit of the invention. Such parameters are chosen to suit the particular use to which the screw is applied.

A screw according to the present invention particularly adapted for use in ankle fusions is shown generally at 410 in FIGS. 21a–b. Screw 410 includes a root portion 412 that tapers at a constant rate from a leading end 414 to a trailing end 416. In the preferred embodiment the root has a length of 2.383-inches and tapers from a radius of 0.184-inches near the trailing end to a radius of 0.098-inches near the leading end.

A screw thread 418 is formed on root portion 412 and extends from the leading end to the trailing end thereof. Thread 418 has a thread crest 420 at its radial outermost edge. As with the previously described embodiments, the thread is terminated at the leading end and trailing end with a 45-degree taper. Thread 418 has a pitch measured between consecutive thread crests which varies between a larger value near the leading end to a smaller value near the trailing end. Preferably, the pitch changes uniformly between the ends from a value of 0.097-inches at the leading end to a value of 0.066-inches at the trailing end.

In contrast to the previously described screws, screw 410 has a guide taper 422 at the leading end of the root portion. The guide taper has a taper angle of approximately 15-degrees and serves to help maintain the leading end of the screw centered in the pilot hole in the bone in which it is installed. The guide taper extends along the root portion back from the 45-degree taper for a distance of 0.129-inches.

Screw 410 has a region 424 of constant outside diameter that extends back from the guide taper for a length of 0.090-inches with a diameter of 0.205-inches. A second region 426 of constant diameter is disposed adjacent the trailing end of the screw with a diameter of 0.256-inches for a length of 0.197-inches. Provision of regions 424 and 426 allow screw 410 to have a long length while reducing the amount of taper that would otherwise be required. It is important to maintain the radius as large as possible near the lead end to obtain adequate grip in this region. This is particularly important in the preferred application for screw 410 of ankle fusions because the amount of screw 410 engaged in the tibia may be limited. It is likewise important not to make the radius at the trailing end any larger than necessary to minimize the size of the hole required. The region of constant diameter at the trailing end is also important because it provides a region for gripping the screw during manufacture. Between the regions of constant diameter is a central region 428 in which the pitch and diameter of the screw change together. The central region has a length of 1.870-inches in the preferred embodiment.

A significant difference between screw 410 and the previously described embodiment lies in the formation of the threads. In particular, in the previously described embodiments, the screw thread is cut with a tool with a flat face and outwardly sloping sides. In the previous embodiments, the width of the face determines the spacing between the threads on the root portion, which was therefore constant along the length of the screw. By pulling the tool back from the axis of the screw and adjusting the pitch properly, the thread can be cut with a varying pitch and depth. However, with each pass of the tool along the screw, the tool follows the same longitudinal path in the thread but simply cuts closer to the root portion. The land at the crest is also increased near the leading end to allow for additional pitch gain near the leading end while maintaining a decreasing outside radius.

In screw 410, in contrast, the longitudinal position of the tool along the root portion is changed from pass to pass as the screw is being turned. In particular, in one pass down the screw thread, the tool follows a first path. In a subsequent pass the tool is shifted longitudinally along the screw slightly at the same depth to increase the width of the interthread distance 428 on the root toward the leading end. Cutting the thread in this fashion allows a sharper thread to be produced while still obtaining the desired outside diameter taper and pitch variation. Sharper thread is beneficial because it leaves a smaller track in the bone which leaves more bone for subsequent threads to grip and makes the screw easier to drive in during installation. As with previously described embodiments, it is important that the radius and depth of the threads near the leading end be sufficient to provide a grip on the bone which is comparable to the grip of the threads near the trailing end of the screw.

It should be understood that screw 410 could be manufactured in a variety of lengths to accommodate different size patients. Moreover, for shorter screws, the region of constant outside diameter near the leading end may be eliminated without unduly compromising the grip of the leading threads. It should also be noted that shorter screws will typically taper at a greater angle.

In the actual fusion, a hole is drilled up from the heal through the calcaneous and talus and into the distal end of the tibia. The screw is then driven into the hole to draw the three bones together. With time, the pressure generated by the screw leads to fusion of the bones. The present screw is advantageous for this operation because it can be mounted subsurface since it does not have a head. Furthermore, the screw offers excellent grip and controllable compression when compared with standard lag screws.

Although not shown in FIGS. 21a–b, screw 410 preferably is cannulated to provide improved stability during installation.

Having illustrated and described the principles of our invention in a preferred embodiment thereof, it should be readily apparent to those skilled in the art that the invention can be modified in arrangement and detail without departing from such principles. We claim all modifications coming within the spirit and scope of the accompanying claims.

I claim:

1. A method of joining first and second objects, the method comprising:

providing a headless screw having an elongate root portion, a leading end and a trailing end, the screw further having a screw thread formed over at least a portion of the root portion, the screw thread have a pitch measured between corresponding points on consecutive thread crests which is larger toward the leading end and smaller toward the trailing end, the screw thread further having a diameter which is larger toward the trailing end and smaller toward the leading end;

introducing the leading end of the screw into the first object through a first surface of the first object;

rotating the screw to drive the leading end of the screw forward through the first object and into the second object until the trailing end of the screw is disposed beneath the first surface of the first object with a portion of the screw thread being disposed in each object to thereby secure the two objects together.

2. The method of claim 1, wherein the first and second objects are initially separated by a gap further comprising closing the gap by driving the screw in until the objects are urged together.

3. A method of urging first and second objects toward each other, the method comprising:

providing a screw having an elongate root portion, a leading end and a trailing end, the screw further having a screw thread formed over at least a portion of the root portion, the screw thread having a pitch measured between corresponding points on consecutive thread crests which is larger toward the leading end and smaller toward the trailing end, wherein the pitch varies substantially continuously over at least a portion of the thread, the screw thread further having a diameter which is larger near the trailing end and smaller near the leading end;

introducing the leading end of the screw into the first object through a first surface of the first object;

driving the leading end of the screw forward through the first object and into the second object until the portion of thread having substantially continuously varying pitch is disposed a partially in the first object and partially in the second object.

4. The method of claim 3, wherein the pitch of the screw thread varies substantially continuously over the majority of the screw.

5. The method of claim 3, wherein the diameter of the screw thread increases as the pitch of the screw thread decreases in the portion of the thread having substantially continuously varying pitch.

6. A method of urging first and second objects toward each other, the method comprising:

providing a screw having an elongate root portion, a leading end and a trailing end, the screw further having a screw thread formed over at least part of the root portion and having a pitch measured between corresponding points on consecutive thread crests;

introducing the leading end of the screw into the first object through a first surface of the first object;

driving the leading end of the screw forward through the first object and into the second object until a leading portion of the screw thread is disposed in the second object and a trailing portion of the screw thread is disposed in the first object, where the pitch of the screw thread is larger toward the leading end and smaller toward the trailing end and the diameter of the screw thread varies in each portion and is smaller toward the leading end and larger toward the trailing end.

7. The method of claim 6, wherein the pitch of the screw thread in each portion varies and is larger toward the leading end and smaller toward the trailing end.

8. A method of urging first and second objects toward each other, the method comprising:

providing a screw having an elongate root portion, a leading end and a trailing end, the screw further having a screw thread formed over at least part of the root portion, the screw thread having a pitch measured between corresponding points on consecutive thread crests which is larger toward the leading end and smaller toward the trailing end and a diameter which is smaller toward the leading end and larger toward the trailing end, at least along a first portion of the screw the pitch gradually increases as the diameter gradually decreases;

introducing the leading end of the screw into the first object;

driving the leading end of the screw forward through the first object and into the second object until the leading end of the screw is disposed in the second object and first portion spans a junction between the first and second objects and with part of the first portion of the screw disposed in each object.

9. The method of claim 8, wherein the first and second objects are adjacent pieces of a fractured bone.

10. The method of claim 9, further including the step of boring a hole into the first and second objects.

11. The method of claim 8, further including screwing the screw into the objects until they are drawn together by compression induced by the screw.

12. A method of drawing together first and second bone portions, the method comprising:

boring a hole into both bone portions, where the hole extends through the first bone portion, across a junction between the bone portions and into the second bone portion;

inserting a leading end of a screw into the hole in the first bone portion, where the screw has a pitch measured between corresponding points on consecutive crests of the thread that is larger near the leading end and smaller near the trailing end and which changes substantially continuously over at least a portion of the screw; and screwing the screw into the hole until the portion of the screw with substantially continuously changing pitch is disposed across the junction between the bone portions with a portion of the screw thread being disposed in each object to thereby secure the two objects together.

13. The method of claim 12, wherein the first and second bone portions are individual bones separated by an articulated joint, and further including leaving the screw in place at least until the articulated joint is fused.

14. The method of claim 13, wherein the individual bones are phalanges.

15. The method of claim 13, wherein the articulated joint is the ankle.

16. The method of claim 12, wherein the step of boring a hole into both bone portions comprises the step of using a single drill bit to bore the hole.

17. The method of claim 12, wherein the step of using a single drill bit to bore the hole comprises the step of using a tapered drill bit.

18. The method of claim 12, wherein said method further includes the step of screwing the screw into the hole until the bone portions are drawn together responsive to compression induced by the screw.

19. The method of claim 12, wherein said screw is a headless screw.

20. The method of claim 19, wherein said screw thread is formed on substantially all of said screw.

21. The method of claim 12, wherein said first and second bone portions are potions of the same bone separated by a fracture.

22. A method for drawing together first and second bone portions, said method comprising:

using a drill bit to bore a hole into both bone portions with a central portion of the hole having both bone portions disposed thereacross;

inserting the nose of a screw into the hole, said screw having a thread pitch measured between substantially all corresponding points of consecutive threads which decreases continuously from a leading end to a trailing end of the screw and a root portion having a substantially constant tapered surface which increases continuously from the leading end to the trailing end;

screwing the screw into the hole; and continuing screwing until all of the screw is received within the bore.

23. The method of claim 22, wherein said first and second bone portions are portions of the same bone separated by a fracture.

24. The method of claim 23, wherein the step of using a drill bit to bore the hole comprises the step of using a tapered drill bit.

25. The method of claim 23, wherein said method further includes the step of screwing the screw into the hole until it is received in both bone portions and the bone portions are drawn together responsive to compression induced by the screw.

26. The method of claim 23, wherein said screw is a headless screw and wherein said root portion trailing end comprises the rearmost portion of said screw.

27. The method of claim 26, wherein said screw thread is formed on substantially all of said root portion.

28. A method for using a screw having a thread pitch measured between substantially all corresponding points of consecutive threads which decreases continuously from a leading end to a trailing end of the screw, said method comprising the steps of:

boring axial holes into first and second bone portions;

inserting the nose of the screw into an end of one of the holes;

screwing the screw into the holes; and stopping screwing when the thread is received in both holes.

29. The method of claim 28, wherein the step boring axial holes into first and second bone portions comprises the step of using a single drill bit to bore the holes.

30. The method of claim 29, wherein the step of using a single drill bit to bore the holes comprises the step of using a tapered drill bit.

31. The method of claim 28, wherein said method further comprises the step of screwing the screw until the screw is entirely received within the axial holes.

32. The method of claim 31, wherein the step of stopping screwing when the thread is received in both holes further comprises the step of stopping screwing when the bone portions are drawn together responsive to compression induced by the screw.

33. The method of claim 28, wherein said screw further includes a tapered root.

34. The method of claim 33, wherein said screw is a headless screw and wherein said root portion trailing end comprises the rearmost portion of said screw.

35. The method of claim 34, wherein said screw thread is formed on substantially all of said root portion.

* * * * *

UNITED STATES PATENT AND TRADEMARK OFFICE
CERTIFICATE OF CORRECTION

PATENT NO. : 5,964,768
DATED : October 12, 1999
INVENTOR(S) : Randall J. Huebner It is certified that error appears in the above-indentified patent and that said Letters Patent is hereby corrected as shown below:

On the title page, item [54] and Column 1:

In the title:

Please replace "TAPERED BONE SCREW WITH CONTINUOUSLY VARYING PITCH" with --METHOD OF SECURING OBJECTS TOGETHER WITH A VARIABLE PITCH SCREW--.

Signed and Sealed this

Nineteenth Day of December, 2000

Attest:

Q. TODD DICKINSON

Attesting Officer

Commissioner of Patents and Trademarks